United States Patent
Govindan et al.

(10) Patent No.: US 7,591,994 B2
(45) Date of Patent: *Sep. 22, 2009

(54) CAMPTOTHECIN-BINDING MOIETY CONJUGATES

(75) Inventors: Serengulam V. Govindan, Summit, NJ (US); David M. Goldenberg, Mendham, NJ (US); Sung-Ju Moon, Denville, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/026,811

(22) Filed: Feb. 6, 2008

(65) Prior Publication Data

US 2008/0166363 A1 Jul. 10, 2008

Related U.S. Application Data

(63) Continuation-in-part of application No. 11/388,032, filed on Mar. 23, 2006, which is a continuation-in-part of application No. 10/734,589, filed on Dec. 15, 2003.

(60) Provisional application No. 60/433,017, filed on Dec. 13, 2002, provisional application No. 60/668,603, filed on Apr. 6, 2005, provisional application No. 60/728,292, filed on Oct. 19, 2005, provisional application No. 60/751,196, filed on Dec. 16, 2005.

(51) Int. Cl.
*A61K 39/395* (2006.01)

(52) U.S. Cl. ............... 424/1.49; 424/178.1; 424/179.1; 424/181.1

(58) Field of Classification Search ................ 424/1.49, 424/178.1, 179.1, 181.1
See application file for complete search history.

(56) References Cited

U.S. PATENT DOCUMENTS

| 6,214,345 B1 * | 4/2001 | Firestone et al. ......... 424/178.1 |
| 2004/0001838 A1 * | 1/2004 | Zhao et al. ............... 424/178.1 |
| 2006/0142506 A1 * | 6/2006 | Breitenkamp et al. ....... 525/482 |

FOREIGN PATENT DOCUMENTS

WO    WO 2004/054622 A1 *   4/2004

OTHER PUBLICATIONS

Walker et al. (Bioorganic and Medicinal Chemistry Letters 2002; 12: 217-219).*
Hatzakis et al. (Chem. Communication, 2006; 2012-2014).*
Suzuwa et al. (J. Controlled Release 2002; 79: 229-242).*
Suzawa et al. (Bioorganic & Medicinal Chemistry 2000; 8: 2175-2184).*

* cited by examiner

*Primary Examiner*—Brandon J Fetterolf
(74) *Attorney, Agent, or Firm*—Richard A. Nakashima

(57) ABSTRACT

The invention relates to therapeutic conjugates with improved ability to target various diseased cells containing a targeting moiety (such as an antibody or antibody fragment), a linker and a camptothecin as a therapeutic moiety, and further relates to processes for making and using the said conjugates.

14 Claims, 6 Drawing Sheets

Cell Binding of Various hMN14-SN38 Immunoconjugates on a Human Colorectal Adenocarcinoma Cell-Line (LoVo)

SEQUENCE LISTING

<160> NUMBER OF SEQ ID NOS: 4

<210> SEQ ID NO 1
<211> LENGTH: 44
<212> TYPE: PRT
<213> ORGANISM: Artificial
<220> FEATURE:
<223> OTHER INFORMATION: synthetic peptide

<400> SEQUENCE: 1

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 2
<211> LENGTH: 45
<212> TYPE: PRT
<213> ORGANISM: Artificial
<220> FEATURE:
<223> OTHER INFORMATION: synthetic peptide

<400> SEQUENCE: 2

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 3
<211> LENGTH: 16
<212> TYPE: PRT
<213> ORGANISM: Artificial
<220> FEATURE:
<223> OTHER INFORMATION: synthetic peptide

<400> SEQUENCE: 3

Gln Ile Glu Tyr Leu Ala Lys Gln Ile Val Asp Asn Ala Ile Gln Gln
1               5                   10                  15

<210> SEQ ID NO 4
<211> LENGTH: 21
<212> TYPE: PRT
<213> ORGANISM: Artificial
<220> FEATURE:
<223> OTHER INFORMATION: synthetic peptide

<400> SEQUENCE: 4

Cys Gly Gln Ile Glu Tyr Leu Ala Lys Gln Ile Val Asp Asn Ala Ile
1               5                   10                  15

Gln Gln Ala Gly Cys
            20

CAMPTOTHECIN-BINDING MOIETY CONJUGATES

RELATED APPLICATIONS

This application is a continuation-in-part of U.S. patent application Ser. No. 11/388,032, filed Mar. 23, 2006, which claimed the benefit under 35 USC 119(e) of provisional U.S. patent application Ser. Nos. 60/668,603, filed Apr. 6, 2005; 60/728,292, filed Oct. 19, 2005 and 60/751,196, filed Dec. 16, 2005; and which was a continuation-in-part of U.S. patent application Ser. No. 10/734,589, filed Dec. 15, 2003, which claimed the benefit under 35 USC 119(e) of provisional U.S. patent application Ser. No. 60/433,017, filed Dec. 13, 2002. The text of each of the priority applications is incorporated herein by reference in its entirety.

FIELD OF THE INVENTION

The present invention relates to therapeutic conjugates with improved ability to target various cancer cells, infectious disease organisms and/or for treating autoimmune diseases, which conjugates contain a targeting (binding) moiety and a therapeutic moiety belonging to the camptothecin group of drugs. The targeting and therapeutic moieties are linked via an intracellularly cleavable linkage that increases therapeutic efficacy.

BACKGROUND OF THE INVENTION

For many years it has been an aim of scientists in the field of specifically targeted drug therapy to use monoclonal antibodies (MAbs) for the specific delivery of toxic agents to human cancers. Conjugates of tumor-associated MAbs and suitable toxic agents have been developed, but have had mixed success in the therapy of cancer, and virtually no application in other diseases, such as infectious and autoimmune diseases. The toxic agent is most commonly a chemotherapy drug, although particle-emitting radionuclides, or bacterial or plant toxins have also been conjugated to MAbs, especially for the therapy of cancer (Sharkey and Goldenberg, C A Cancer J Clin. 2006 July-August; 56(4):226-243) and, more recently, with radioimmunoconjugates for the preclinical therapy of certain infectious diseases (Dadachova and Casadevall, Q J Nucl Med Mol Imaging 2006; 50(3): 193-204; incorporated herein by reference in its entirety).

The advantages of using MAb-chemotherapy drug conjugates are that (a) the chemotherapy drug itself is structurally well defined; (b) the chemotherapy drug is linked to the MAb protein using very well defined conjugation chemistries, often at specific sites remote from the MAbs antigen binding regions; (c) MAb-chemotherapy drug conjugates can be made more reproducibly than chemical conjugates involving MAbs and bacterial or plant toxins, and as such are more amenable to commercial development and regulatory approval; and (d) the MAb-chemotherapy drug conjugates are orders of magnitude less toxic systemically than radionuclide MAb conjugates.

The present disclosure solves specific problems associated with the preparation of conjugates of the camptothecin (CPT) group of cytotoxic compounds. CPT and its derivatives are a class of potent antitumor agents. Irinotecan (also referred to as CPT-11) and topotecan are CPT analogs that are approved cancer therapeutics (Iyer and Ratain, Cancer Chemother. Phamacol. 42: S31-S43 (1998)). CPTs act by inhibiting topoisomerase I enzyme by stabilizing topoisomerase I-DNA complex (Liu, et al. in *The Camptothecins: Unfolding Their Anticancer Potential*, Liehr J. G., Giovanella, B. C. and Verschraegen (eds), NY Acad Sci., NY 922:1-10 (2000)).

CPTs present a set of caveats in the preparation of conjugates. One caveat is the insolubility of most CPT derivatives in aqueous buffers. Secondly, CPTs provide specific challenges for structural modification for conjugating to macromolecules. For instance, CPT itself contains only a tertiary hydroxyl group in ring-E. The hydroxyl functional group in the case of CPT must be coupled to a linker suitable for subsequent protein conjugation; and in potent CPT derivatives, such as SN-38, the active metabolite of the chemotherapeutic CPT-11, and other C-10-hydroxyl-containing derivatives such as topotecan and 10-hydroxy-CPT, the presence of phenolic hydroxyl at C-10 position complicates the necessary C-20-hydroxyl derivatization. Thirdly the lability of the δ-lactone moiety of the E-ring of their structures, under physiological conditions, results in greatly reduced antitumor potency of these products. Therefore, the conjugation protocol is performed such that it is carried out at a pH of 7 or lower to avoid the lactone ring opening. Typically conjugation of a bifunctional CPT possessing an amine-reactive group such as an active ester would require a pH of 8 or greater. Fourth, an intracellularly-cleavable moiety is to be incorporated in the linker/spacer connecting the CPTs and the antibodies or other binding moieties.

The problem of δ-lactone opening under physiological conditions has been previously addressed. One approach has been to acylate the C-20 hydroxyl group with an amino acid, and couple the α-amino group of the amino acid to poly-L-glutamic acid (Singer et al. in *The Camptothecins: Unfolding Their Anticancer Potential*, Liehr J. G., Giovanella, B. C. and Verschraegen (eds), NY Acad Sci., NY 922:136-150 (2000)). This approach relies on the passive diffusion of a polymeric molecule into tumor sites. This glycine conjugation has also been reported as a method of making water-soluble derivative of CPT (Vishnuvajjala et al., U.S. Pat. No. 4,943,579) and in the preparation of a PEG-derivatization of CPT (Greenwald, et al. *J. Med. Chem.* 39: 1938-1940 (1996)). In the latter case, the approach has been devised in the context of developing water-soluble and long acting forms of CPT, whereby CPT's in vivo half-life is enhanced, and the drug is gradually released from its conjugate while in circulation in vivo.

The present invention discloses methods for preparing conjugates of CPTs, of 10-hydroxy derivatives such as SN-38 in particular, taking into consideration the four caveats described above and the synthetic challenges. SN-38 is the active drug form of the approved cancer drug CPT-11, which is a prodrug. Vast clinical data are available concerning CPT-11 pharmacology and of its in vivo conversion to SN-38 (Iyer and Ratain, supra; Mathijssen et al., *Clin Cancer Res.* 7:2182-2194 (2002); Rivory, *Ann NY Acad Sci.* 922:205-215, 2000)). The active form SN-38 is about 2 to 3 orders of magnitude more potent than CPT-11.

Early work on protein-drug conjugates indicated that a drug ideally needed to be released in its original form, once it had been internalized into a target cell, for the protein-chemotherapy drug conjugate to be a useful therapeutic. Trouet et al. (*Proc. Natl. Acad. Sci. USA* 79:626-629 (1982)) showed the advantage of using specific peptide linkers, between the drug and the targeting moiety, which are cleaved lysosomally to liberate the intact drug. Work during the 1980's and early 1990's focused further on the nature of the chemical linker between the chemotherapeutic drug and the MAb. Notably, MAb-chemotherapy drug conjugates prepared using mild acid-cleavable linkers were developed, based on the observation that the pH inside tumors was often lower than normal physiological pH. In this respect, superior results were found by incorporating a hydrazone as a cleavable unit, and attaching DOX to a MAb via a thioether group, (Willner et al., U.S. Pat. No. 5,708,146; Trail et al. (*Science* 261:212-215 (1993)).

This approach showed that MAb-doxorubicin (DOX) conjugates, prepared with appropriate linkers, could be used to cure mice bearing a variety of human tumor xenografts, in preclinical studies. The first approved MAb-drug conjugate, Gemtuzumab Ozogamicin, incorporates a similar acid-labile hydrazone bond between an anti-CD33 antibody, humanized P67.6, and a potent calicheamicin derivative. Sievers et al., *J Clin Oncol*. 19:3244-3254 (2001); Hamann et al., *Bioconjugate Chem*. 13: 47-58 (2002). In some cases, the MAb-chemotherapy drug conjugates were made with reductively labile hindered disulfide bonds between the chemotherapy drugs and the MAb (Liu et al., *Proc Natl Acad Sci USA* 93: 8618-8623 (1996)). Yet another cleavable linker involves a cathepsin B-labile dipeptide spacers, such as Phe-Lys or Val-Cit, similar to the lysosomally labile peptide spacers of Trouet et al. containing from one to four amino acids, which additionally incorporated a collapsible spacer between the drug and the dipeptide (Dubowchik, et al., *Bioconjugate Chem*. 13:855-869 (2002); Firestone et al., U.S. Pat. No. 6,214,345 B1; Doronina et al., *Nat. Biotechnol*. 21: 778-784 (2003)). The latter approaches were also utilized in the preparation of an immunoconjugate of camptothecin (Walker et al., *Bioorg Med Chem Lett*. 12:217-219 (2002)). Another cleavable moiety that has been explored is an ester linkage incorporated into the linker between the antibody and the chemotherapy drug. Gillimard and Saragovi have found that when an ester of paclitaxel was conjugated to anti-rat p75 MAb, MC192, or anti-human TrkA MAb, 5C3, the conjugate was found to exhibit target-specific toxicity. Gillimard and Saragovi, *Cancer Res*. 61:694-699 (2001).

While the importance of cleavable linker in the design of binding moiety-drug conjugates cannot be overstated, it is also important to focus on how the linker design impacts the overall preparation of specific CPT-binding moiety conjugates. The present invention solves the problem associated with the preparation of the bifunctional drug-linker molecule, wherein the said drug may also contain more than one reactive group for derivatization, such as the potent SN-38 analog, for instance, in the design of conjugates. SN-38, a clinically important active drug form of the cancer drug CPT-11, but 100-1000-times more potent than CPT-11, is not useable systemically because of insolubility. The present invention solves this problem by conjugating it to a targeting moiety in ways that also address other challenges of using a CPT, while concurrently improving the therapeutic index of this clinically important potent drug by using disease-specific antibodies.

The conjugates of the instant invention possess greater efficacy, in many cases, than unconjugated or "naked" antibodies or antibody fragments, although such unconjugated targeting molecules have been of use in specific situations. In cancer, for example, naked antibodies have come to play a role in the treatment of lymphomas (CAMPATH® and RITUXAN®), colorectal and other cancers (ERBITUX® and AVASTIN®), breast cancer (HERECEPTIN®), as well as a large number now in clinical development (e.g., epratuzumab). In most of these cases, clinical use has involved combining these naked, or unconjugated, antibodies with other therapies, such as chemotherapy or radiation therapy.

A variety of antibodies are also in use for the treatment of autoimmune and other immune dysregulatory diseases, such as tumor necrosis factor (TNF) and B-cell (RITUXAN®) antibodies in arthritis, and are being investigated in other such diseases, such as the B-cell antibodies, RITUXAN® and epratuzumab, in systemic lupus erythematosus and Sjögren's syndrome, as well as juvenile diabetes and multiple sclerosis. Naked antibodies are also being studied in sepsis and septic shock, Alzheimer's disease, and infectious diseases. The development of anti-infective monoclonal antibodies has been reviewed recently by Reichert and Dewitz (Nat Rev Drug Discovery 2006; 5:191-195), incorporated herein by reference, which summarizes the priority pathogens against which naked antibody therapy has been pursued, resulting in only 2 pathogens against which antibodies are either in Phase III clinical trials or are being marketed (respiratory syncytial virus and methicillin-resistant *Staphylococcus aureus*), with 25 others in clinical studies and 20 discontinued during clinical study.

Thus, there is a need to develop more potent anti-pathogen antibodies and other binding moieties. Such antibody-mediated therapeutics can be developed for the treatment of many different pathogens, including bacteria, fungi, viruses, and parasites, either as naked (unconjugated), radiolabeled, or drug/toxin conjugates. In the case of delivering drug/toxin or radionuclide conjugates, this can be accomplished by direct antibody conjugation or by indirect methods, referred to as pretargeting, where a bispecific antibody is used to target to the lesion, while the therapeutic agent is secondarily targeted by binding to one of the arms of the bispecific antibody that has localized at the site of the pathogen or of the cancer or whatever lesion is being treated (discussed by Goldenberg et al., J Clin Oncol. 2006 February 10; 24(5):823-34; and Goldenberg et al., J Nucl Med. 2008 January; 49(1):158-63, both incorporated in their entirety herein by reference).

SUMMARY OF THE INVENTION

The present invention resolves an unfulfilled need in the art by providing improved methods and compositions for preparation of camptothecin-binding moiety conjugates. The disclosed methods and compositions are of use for the treatment of a variety of diseases and conditions which are refractory or less responsive to other forms of therapy, and can include diseases against which suitable targeting (binding) moieties for selective targeting can be developed, or are available or known. Preferably, the targeting moiety is an antibody, antibody fragment, bispecific or other multivalent antibody, or other antibody-based molecule or compound. The antibody can be of various isotypes, preferably IgG1, IgG2a, IgG3, IgG4, and IgA, and can be a chimeric human-mouse, a chimeric human-primate, a humanized (human framework and murine hypervariable (CDR) regions), or fully human MAbs, as well as variations thereof, such as half-IgG4 antibodies, referred to as "Unibodies," as described by van der Neut Kolfschoten et al. (*Science* 2007; 317:1554-1557), incorporated herein by reference in its entirety. However, other binding moieties known in the art, such as aptamers, avimers or targeting peptides, may be used. Preferred diseases or conditions against which such targeting moieties exist are, for example, cancer, immune dysregulatory conditions, including autoimmune diseases and inflammatory diseases, and diseases caused by infectious organisms.

The disclosed methods and compositions may thus be applied for treatment of diseases and conditions for which targeting moieties are of use to deliver camptothecin-related cytotoxic agents. Such diseases or conditions may be characterized by the presence of a target molecule or target cell that is insufficiently affected when unconjugated, or naked, targeting moieties are used, such as in the immunotherapy of cancer or of infection with pathogenic organisms. (For methods of making immunoconjugates of antibodies with isotopes, drugs, and toxins for use in disease therapies, see, e.g., U.S. Pat. Nos. 4,699,784; 4,824,659; 5,525,338; 5,677,427; 5,697,902; 5,716,595; 6,071,490; 6,187,284; 6,306,393; 6,653,104; 6,962,702; and U.S. Patent Appln. Publ. Nos. 20050191239; 20050175582; 20050136001; 20040166115; 20040043030; 20040022725; 20030068322; 20030031669; 20030026764 and 20020136690, each incorporated by reference in its entirety.)

In certain exemplary embodiments, camptothecin conjugates of antibodies or antibody fragments may be used for targeting this therapeutic drug to pathogens, such as bacteria, viruses, fungi, and parasites. In preferred embodiments, such drug-conjugated targeting moieties can be used in combination with other therapeutic modalities, such as anti-fungal, antibiotics and anti-viral drugs and/or naked antibodies, immunomodulators (e.g., interferon, interleukins and/or other cytokines). The use of radioimmunotherapy for the treatment of infectious organisms is disclosed, for example, in U.S. Pat. Nos. 4,925,648; 5,332,567; 5,439,665; 5,601,825; 5,609,846; 5,612,016; 6,120,768; 6,319,500; 6,458,933; 6,548,275; and in U.S. Patent Application Publication Nos. 20020136690 and 20030103982, each of which is incorporated herein by reference in its entirety.

In certain embodiments involving treatment of cancer, the camptothecin conjugates may be used in combination with surgery, radiation, chemotherapy, immunotherapy with naked antibodies, radioimmunotherapy, immunomodulators, vaccines, and the like. Similar combinations are preferred in the treatment of the other diseases amenable to targeting moieties, such as autoimmune diseases. For example, the camptothecin conjugates can be combined with TNF inhibitors, B-cell antibodies, interferons, interleukins, and other effective agents for the treatment of autoimmune diseases, such as rheumatoid arthritis, systemic lupus erythematosis, Sjögren's syndrome, multiple sclerosis, vasculitis, as well as type-I diabetes (juvenile diabetes). These combination therapies can allow lower doses of each therapeutic to be given in such combinations, thus reducing certain severe side effects, and potentially reducing the courses of therapy required. In viral diseases, these drug immunoconjugates can be combined with other therapeutic drugs, immunomodulators, naked MAbs, or vaccines (e.g., MAbs against hepatitis, HIV, or papilloma viruses, or vaccines based on immunogens of these viruses). Antibodies and antigen-based vaccines against these and other viral pathogens are known in the art and, in some cases, already in commercial use.

In one embodiment, the invention relates to a process of preparing conjugates, wherein a CPT drug is first derivatized with a linker, which said linker contains a reactive moiety that is capable of combining with a second linker that additionally contains a targeting-moiety-coupling group; wherein the first linker also possesses a defined polyethylene glycol (PEG) moiety for water-solubility, and optionally an intracellularly-cleavable moiety cleavable by intracellular peptidases or cleavable by the low pH environment of endosomal and lysosomal vesicles, and optionally an amino acid spacer between the said drug and the first linker; wherein the second linker contains a reactive group capable of reacting with drug-(first linker) conjugate by the copper (+1) ion-catalyzed acetylene-azide cycloaddition reaction, referred to as 'click chemistry' in the art.

In another embodiment, the invention relates to a process of preparing conjugates as given in the paragraph above, wherein the second linker has a single targeting-moiety-coupling group, but multiples of the reactive group capable of reacting with drug-(first linker) conjugate, thereby amplifying the number of drug molecules conjugated to the targeting moiety.

In a further embodiment, the invention relates to a process of preparing conjugates, wherein the linker is first conjugated to a CPT drug, thereby producing a CPT drug-linker conjugate; wherein said CPT drug-linker conjugate preparation involves the selective protection and deprotection of C-10 hydroxyl group, keeping the C-20 carbonate bond essentially intact, in derivatives of CPT containing a C-10 hydroxyl group; wherein said drug-linker conjugate is optionally not purified; and wherein said drug-linker conjugate is subsequently conjugated to a monoclonal antibody or fragment.

Yet another embodiment of the invention is a method of treating cancer (a malignancy), an autoimmune disease, an infection, or an infectious lesion with the conjugates described herein. Alternative embodiments concern the drug-targeting moiety conjugates made by the claimed processes and/or kits for performing the claimed processes.

BRIEF DESCRIPTION OF THE DRAWINGS

The following drawings form part of the present specification and are included to further demonstrate certain aspects of particular embodiments of the invention. The embodiments may be better understood by reference to one or more of these drawings in combination with the detailed description presented herein.

DEFINITIONS

Figure 1:
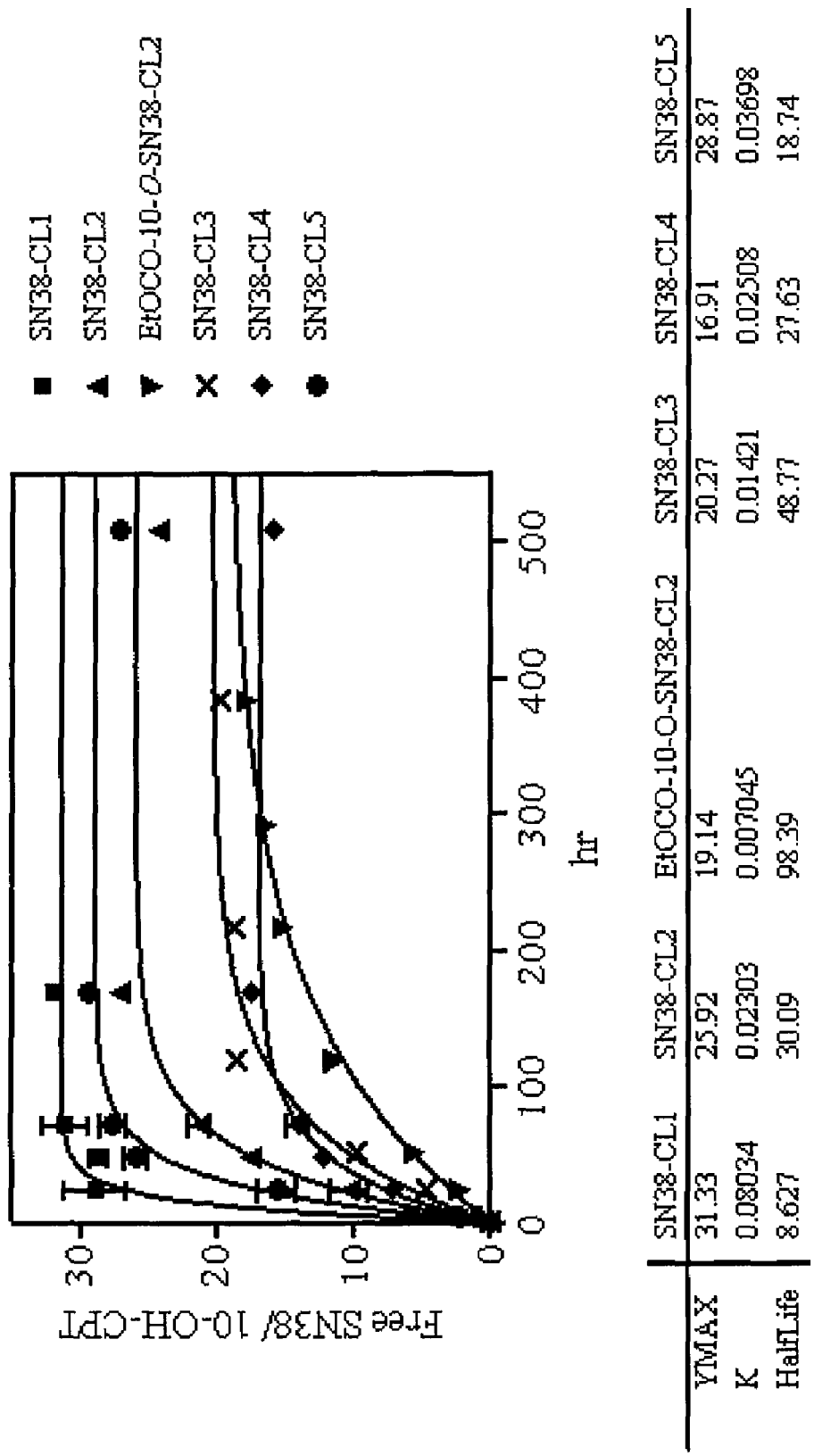
FIG. 1. Hydrolytic stability of hMN-14-[SN38-CL'x'] ('x'=1, 2, 3, 4, 5) and hMN-14-[EtO-CO-10-O-SN38-CL2] conjugates in PBS, pH 7.4, 37° C.

Unless otherwise specified, "a" or "an" means "one or more."

In the description that follows, a number of terms are used and the following definitions are provided to facilitate understanding of the present invention. Terms that are not expressly defined herein are used in accordance with their plain and ordinary meanings.

The term targeting moiety as used herein refers to a molecule, complex or aggregate, that binds specifically or selectively to a target molecule, cell, particle, tissue or aggregate. In preferred embodiments, a targeting moiety is an antibody, antibody fragment, bispecific antibody or other antibody-based molecule or compound. However, other examples of targeting moieties are known in the art and may be used, such as aptamers, avimers, receptor-binding ligands, nucleic acids, biotin-avidin binding pairs, binding peptides or proteins, etc. The terms "targeting moiety" and "binding moiety" are used synonymously herein.

An antibody, as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment. An antibody or antibody fragment may be conjugated or otherwise derivatized within the scope of the claimed subject matter. Such antibodies include IgG1, IgG2a, IgG3, IgG4 (and IgG4 subforms), as well as IgA isotypes.

An antibody fragment is a portion of an antibody such as F(ab')$_2$, F(ab)$_2$, Fab', Fab, Fv, scFv (single chain Fv) and the like, including the half-molecules of IgG4 cited above (van der Neut Kolfschoten et al. (Science 2007; 317(14 September):1554-1557). Regardless of structure, an antibody fragment of use binds with the same antigen that is recognized by the intact antibody. The term "antibody fragment" also includes any synthetic or genetically engineered protein that acts like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region, such as CDRs. The Fv fragments may be constructed in different ways to yield multivalent and/or multispecific binding forms. In the former case of multivalent, they react with more than one binding site against the specific epitope, whereas with multispecific forms, more than one epitope (either of the same antigen or against the specific antigen and a different antigen) is bound. As used herein, the term antibody component includes an entire antibody, a fusion protein, and fragments thereof.

A naked antibody is generally an entire antibody that is not conjugated to a therapeutic agent. This is so because the Fc portion of the antibody molecule provides effector or immunological functions, such as complement fixation and ADCC (antibody-dependent cell cytotoxicity), which set mechanisms into action that may result in cell lysis. However, the Fc portion may not be required for therapeutic function of the antibody, but rather other mechanisms, such as apoptosis, anti-angiogenesis, anti-metastatic activity, anti-adhesion activity, such as inhibition of heterotypic or homotypic adhesion, and interference in signaling pathways, may come into play and interfere with the disease progression. Naked antibodies include both polyclonal and monoclonal antibodies, and fragments thereof, that include murine antibodies, as well as certain recombinant antibodies, such as chimeric, humanized or human antibodies and fragments thereof. Therefore, in some cases a "naked antibody" may also refer to a "naked" antibody fragment. As defined herein, "naked" is synonymous with "unconjugated," and means not linked or conjugated to a therapeutic agent with which it administered.

Autoimmune Diseases are disorders that are caused by the body producing an immune response against its own tissues. Examples include Class III autoimmune diseases such as immune-mediated thrombocytopenias, acute idiopathic thrombocytopenic purpura and chronic idiopathic thrombocytopenic purpura, dermatomyositis, Sjögren's syndrome, multiple sclerosis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, sarcoidosis, ulcerative colitis, erythema multiforme, IgA nephropathy, polyarteritis nodosa, ankylosing spondylitis, Goodpasture's syndrome, thromboangitis ubiterans, Sjogren's syndrome, primary biliary cirrhosis, Hashimoto's thyroiditis, thyrotoxicosis, scleroderma, chronic active hepatitis, rheumatoid arthritis, polymyositis/dermatomyositis, polychondritis, pamphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis, as disclosed in U.S. Provisional Application Ser. No. 60/360,259, filed Mar. 1, 2002, incorporated herein by reference in its entirety.

A chimeric antibody is a recombinant protein that contains the variable domains of both the heavy and light antibody chains, including the complementarity determining regions (CDRs) of an antibody derived from one species, preferably a rodent antibody, more preferably a murine antibody, while the constant domains of the antibody molecule are derived from those of a human antibody. For veterinary applications, the constant domains of the chimeric antibody may be derived from that of other species, such as a subhuman primate, cat or dog.

A humanized antibody is a recombinant protein in which the CDRs from an antibody from one species; e.g., a rodent antibody, are transferred from the heavy and light variable chains of the rodent antibody into human heavy and light variable domains. The constant domains of the antibody molecule are derived from those of a human antibody. In some cases, specific residues of the framework region of the humanized antibody, particularly those that are touching or close to the CDR sequences, may be modified, for example replaced with the corresponding residues from the original rodent, subhuman primate, or other antibody.

A human antibody is an antibody obtained, for example, from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994). A fully human antibody also can be constructed by genetic or chromosomal transfection methods, as well as phage display technology, all of which are known in the art. See for example, McCafferty et al., *Nature* 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g. Johnson and Chiswell, *Current Opinion in Structural Biology* 3:5564-571 (1993). Human antibodies may also be generated by in vitro activated B cells. See U.S. Pat. Nos. 5,567,610 and 5,229,275, which are incorporated herein by reference in their entirety.

Infectious Diseases as used herein are diseases involving infection by pathogens such as bacteria, rickettsia, mycoplasma, protozoa, fingi, viruses, parasites, or other microbial agents. Examples include human immunodeficiency virus (HIV) causing AIDS, *Mycobacterium* of tuberculosis, *Streptococcus agalactiae*, methicillin-resistant *Staphylococcus aureus*, *Legionella pneumophilia*, *Streptococcus pyogenes*, *Escherichia coli*, *Neisseria gonorrhosae*, *Neisseria meningitidis*, *Pneumococcus*, *Cryptococcus neoformans*, *Histoplasma capsulatum*, *Hemophilis influenzae* B, *Treponema pallidum*, Lyme disease spirochetes, West Nile virus, *Pseudomonas aeruginosa*, *Mycobacterium leprae*, *Brucella abortus*, rabies virus, influenza virus, cytomegalovirus, herpes simplex virus I, herpes simplex virus II, human serum parvo-like virus, respiratory syncytial virus, varicella-zoster virus, hepatitis B virus, hepatitis C virus, measles virus, adenovirus, human T-cell leukemia viruses, Epstein-Barr virus, murine leukemia virus, mumps virus, vesicular stomatitis virus, sindbis virus, lymphocytic choriomeningitis virus, wart virus, blue tongue virus, Sendai virus, feline leukemia virus, reo virus, polio virus, simian virus 40, mouse mammary tumor virus, dengue virus, rubella virus, *Plasmodium falciparum*, *Plasmodium vivax*, *Toxoplasma gondii*, *Trypanosoma rangeli*, *Trypanosoma cruzi*, *Trypanosoma rhodesiensei*, *Trypanosoma brucei*, *Schistosoma mansoni*, *Schistosoma japanicum*, *Babesia bovis*, *Elmeria tenella*, *Onchocerca volvulus*, *Leishmania tropica*, *Trichinella spiralis*, *Theileria parva*, *Taenia hydatigena*, *Taenia ovis*, *Taenia saginata*, *Echinococcus granulosus*, *Mesocestoides corti*, *Mycoplasma arthritidis*, *M. hyorhinis*, *M. orale*, *M. arginini*, *Acholeplasma laidlawii*, *M. salivarium* and *M. pneumoniae*. A review listing antibodies against infectious organisms (antitoxin and antiviral antibodies), as well as other targets, is contained in Casadevall, Clin Immunol 1999; 93(1):5-15, incorporated herein by reference in its entirety.

A therapeutic agent is a molecule or atom that is administered separately, concurrently or sequentially with a binding moiety, e.g., an antibody or antibody fragment, or a subfragment thereof, and is useful in the treatment of a disease. Examples of therapeutic agents include, but are not limited to, antibodies, antibody fragments, conjugates, drugs, cytotoxic agents, proapoptotic agents, toxins, nucleases (including DNAses and RNAses), hormones, immunomodulators, chelators, boron compounds, photoactive agents or dyes, radioisotopes or radionuclides, oligonucleotides, interference RNA, peptides, anti-angiogenic agents, chemotherapeutic agents, cyokines, chemokines, prodrugs, enzymes, binding proteins or peptides, conjugates or combinations thereof.

A conjugate is an antibody component or other targeting moiety conjugated to a therapeutic agent. Suitable therapeutic agents are described above.

As used herein, the term antibody fusion protein is a recombinantly-produced antigen-binding molecule in which two or more of the same or different natural antibody, single-chain antibody or antibody fragment segments with the same or different specificities are linked. A fusion protein comprises at least one specific binding site. Valency of the fusion protein indicates the total number of binding arms or sites the fusion protein has to antigen(s) or epitope(s); i.e., monovalent, bivalent, trivalent or multivalent. The multivalency of the antibody fusion protein means that it can take advantage of multiple interactions in binding to an antigen, thus increasing the avidity of binding to the antigen, or to different antigens. Specificity indicates how many different types of antigen or epitope an antibody fusion protein is able to bind; i.e., monospecific, bispecific, trispecific, multispecific. Using these definitions, a natural antibody, e.g., an IgG, is bivalent because it has two binding arms but is monospecific because it binds to one type of antigen or epitope. A monospecific, multivalent fusion protein has more than one binding site for the same antigen or epitope. For example, a monospecific diabody is a fusion protein with two binding sites reactive with the same antigen. The fusion protein may comprise a multivalent or multispecific combination of different antibody components or multiple copies of the same antibody component. The fusion protein may additionally comprise a therapeutic agent.

An immunomodulator is a therapeutic agent that when present, alters, suppresses or stimulates the body's immune system. Typically, an immunomodulator of use stimulates immune cells to proliferate or become activated in an immune response cascade, such as macrophages, dendritic cells, B-cells, and/or T-cells. However, in some cases an immunomodulator may suppress proliferation or activation of immune cells, as in therapeutic treatment of autoimmune disease. An example of an immunomodulator as described herein is a cytokine, which is a soluble small protein of approximately 5-20 kDa that is released by one cell population (e.g., primed T-lymphocytes) on contact with specific antigens, and which acts as an intercellular mediator between cells. As the skilled artisan will understand, examples of cytokines include lymphokines, monokines, interleukins, and several related signaling molecules, such as tumor necrosis factor (TNF) and interferons. Chemokines are a subset of cytokines. Certain interleukins and interferons are examples of cytokines that stimulate T cell or other immune cell proliferation.

CPT is abbreviation for camptothecin, and as used in the present application CPT represents camptothecin itself or an analog or derivative of camptothecin. The structures of camptothecin and some of its analogs, with the numbering indicated and the rings labeled with letters A-E, are given in formula 1 in Chart 1 below.

Chart 1

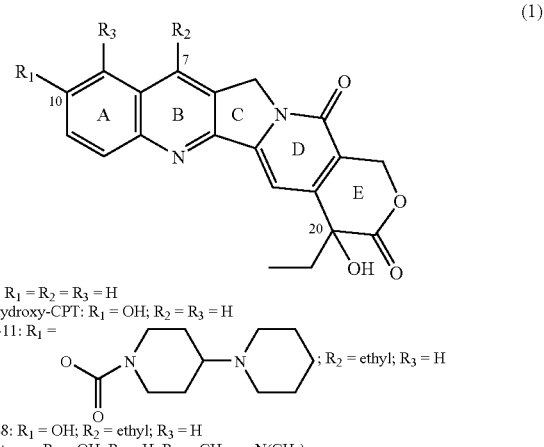

CPT: $R_1 = R_2 = R_3 = H$
10-Hydroxy-CPT: $R_1 = OH; R_2 = R_3 = H$
CPT-11: $R_1 = $ [structure]; $R_2 = $ ethyl; $R_3 = H$
SN-38: $R_1 = OH; R_2 = $ ethyl; $R_3 = H$
Topotecan: $R_1 = OH; R_2 = H; R_3 = CH_2-N(CH_3)_2$

DETAILED DESCRIPTION OF THE INVENTION

Methods are devised in the following ways for the preparation of conjugates of CPT or a CPT analog or derivative (collectively 'CPT') with targeting moiety such as an antibody (MAb). The disclosed methods represent a preferred embodiment of the invention. (1) Solubility of CPT is enhanced by placing a defined polyethylene glycol moiety (PEG) between CPT and the targeting vector; (2) a first linker connects the drug at one end and terminates with an acetylene or an azide or acetylene group at the other end; this first linker comprises a defined PEG moiety with an azide or acetylene group at one end and a different reactive group, such as carboxylic acid or hydroxy group, at the other end and said bifunctional defined PEG is attached to a CPT-20-ester derived from an amino acid or to the CPT-20-O-chloroformate; alternatively, the non-azide (or acetylene) moiety of said defined bifunctional PEG is optionally attached to a cleavable linker, cleavable by intracellular peptidases or by low pH in certain intracellular compartments, and the cleavable linker is attached to the drug; (3) a second linker, comprising a targeting moiety-coupling group and a reactive group complementary to the azide (or acetylene) group of the first linker, namely acetylene (or azide), reacts with the drug-(first linker) conjugate via acetylene-azide cycloaddition reaction to furnish the final bifunctional drug product that is useful for conjugating to the disease targeting moieties such as disease-targeting antibodies; (4) the antibody-coupling group is designed to be either a thiol or a thiol-reactive group; (5) methods are devised for selective regeneration of the 10-hydroxyl group in presence of the C-20 carbonate in preparations of drug-linker precursor involving CPT analogs such as SN-38; and (6) the 10-hydroxyl group of CPT analogs is alternatively protected as an ester or carbonate, other than 'BOC', such that the bifunctional CPT is conjugated to targeting moiety without prior deprotection of this protecting group, and the protecting group is readily deprotected under the physiological pH condition after the bioconjugate is administered. In the acetylene-azide coupling, referred to as 'click chemistry' in the art, the azide part may be on L2 with acetylene part on L3; alternatively, L2 may contain acetylene, with L3 containing azide. 'Click chemistry' is a copper (+1)-catalyzed cycloaddition reaction between an acetylene moiety and an azide moiety, and is a relatively recent technique in bioconjugations (Kolb H C and Sharpless K B, *Drug Discov Today* 2003; 8: 1128-37). Click chemistry takes place in aqueous solution at near-neutral pH conditions, and is thus amenable for drug conjugation. The advantage of click chemistry is that it is chemoselective, and complements other well-known conjugation chemistries such as the thiol-maleimide reaction. In the following discussion, where a conjugate comprises an antibody or antibody fragment, another type of binding moiety, such as an aptamer, avimer or targeting peptide, may be substituted.

An exemplary preferred embodiment is directed to a conjugate of a camptothecin drug derivative and an antibody of the general formula 2, MAb-[L3]-[L2]-[L1]$_m$AA$_n$-CPT     (2)

where MAb is a disease-targeting antibody; CPT is camptothecin (CPT) or an analog thereof; L-3 is a component of the cross-linker comprising an antibody-coupling moiety and one or more of acetylene (or azide) groups; L2 comprises a defined PEG with azide (or acetylene) at one end, complementary to the acetylene (or azide) moiety in linker 3, and a reactive group such as carboxylic acid or hydroxyl group at the other end; L1 comprises a collapsible linker, or a peptidase-cleavable moiety optionally attached to a collapsible linker, or an acid-cleavable moiety; AA is an amino acid; m is an integer with values of 0 or 1, and n is an integer with values of 0, 1, 2, 3, or 4.

In a preferred embodiment, m is 0. In this embodiment, an ester moiety is first formed between the carboxylic acid of an amino acid such as glycine, alanine, or sarcosine, or of a peptide such as glycylglycine, and the 20-hydroxyl of CPT. In these cases, the N-terminus of the amino acid or polypeptide is protected as a Boc or a Fmoc or a monomethoxytrityl (MMT) derivative, which is deprotected after formation of an ester bond with the 20-hydroxyl of CPT. Selective removal of amine-protecting group, in presence of a BOC protecting group at the C-10-hydroxyl position of CPT analogs containing the additional 10-hydroxyl group, as in some analogs shown in Chart 1, is achieved using monomethoxytrityl (MMT) as the protecting group for the amino group of amino acid or polypeptide involved in ester formation, since 'MMT' is removable by mild acid treatment such as dichloroacetic acid that does not cleave a BOC group. After the amino group of the amino acid or polypeptide, forming an ester bond with CPT at the 20 position, is demasked, the amino group is reacted with the activated form of COOH group on PEG moiety of L1 under standard amide-forming conditions. In a preferred embodiment, L3 comprises a thiol-reactive group which links to thiol groups of said targeting moiety. The thiol-reactive group is optionally a maleimide or vinylsulfone, or bromoacetamide, or iodoacetamide, which links to thiol groups of said targeting moiety. In a preferred embodiment, said reagent bearing a thiol-reactive group is generated from succinimidyl-4-(N maleimidomethyl)cyclohexane-1-carboxylate (SMCC) or from succinimidyl-(ε-maleimido)caproate, for instance, with the thiol-reactive group being a maleimide group.

In a preferred embodiment, m is 0, and AA comprises polypeptide moiety, preferably tri or tetrapeptide, that is cleavable by intracellular peptidase such as Cathepsin-B. Examples of cathepsin-B-cleavable peptides are: Phe-Lys, Val-Cit (Dubowchick, 2002), Ala-Leu, Leu-Ala-Leu, and Ala-Leu-Ala-Leu (Trouet et al., 1982).

In a preferred embodiment, L1 is composed of intracellularly-cleavable polypeptide, such as cathepsin-B-cleavable peptide, connected to the collapsible linker p-aminobenzyl alcohol at the peptide's C-terminus, the benzyl alcohol portion of which is in turn directly attached to CPT-20-O-chloroformate. In this embodiment, n is 0. Alternatively, when 'n' is non-zero, the benzyl alcohol portion of the p-amidobenzyl alcohol moiety is attached to the N-terminus of the amino acid or polypeptide linking at CPT's 20 position through the activated form of p-amidobenzyl alcohol, namely PABOCOPNP where PNP is p-nitrophenyl. In a preferred embodiment, the linker comprises a thiol-reactive group which links to thiol groups of said targeting moiety. The thiol-reactive group is optionally a maleimide or vinylsulfone, or bromoacetamide, or iodoacetamide, which links to thiol groups of said targeting moiety. In a preferred embodiment, said reagent bearing a thiol-reactive group is generated from succinimidyl-4-(N maleimidomethyl)cyclohexane-1-carboxylate (SMCC) or from succinimidyl-(ε-maleimido)caproate, for instance, with the thiol-reactive group being a maleimide group.

In a preferred embodiment, the L2 component of the conjugate contains a polyethylene glycol (PEG) spacer that can be of up to MW 5000 in size, and in a more preferred embodiment, PEG is a defined PEG with (1-12 or 1-30) repeating monomeric units. In a further preferred embodiment, PEG is a defined PEG with 1-12 repeating monomeric units. The introduction of PEG may involve using heterobifunctionalized PEG derivatives which are available commercially. In the context of the present invention, the heterobifunctional PEG contains an azide or acetylene group. An example of a heterobifunctional defined PEG containing 8 repeating monomeric units, with 'NHS' being succinimidyl, is given below in formula 3:

(3)

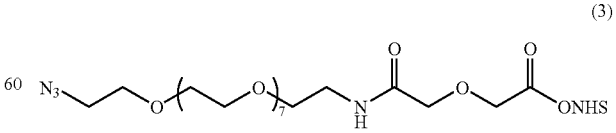

In a preferred embodiment, L3 has a plurality of acetylene (or azide) groups, ranging from 2-40, but preferably 2-20, and more preferably 2-5, and a single targeting vector-binding moiety.

A representative SN-38 (a CPT analog) conjugate of an antibody, prepared with a maleimide-containing SN-38-linker derivative, with the bonding to MAb represented as a succinimide, is given below. Here, m=0, and the 20-O-AA ester bonding to SN-38 is glycinate; azide-acetylene coupling joining the L2 and L3 parts of formula 2 results in the triazole moiety as shown.

lSN-38 as a carbonate bonding at the 20 position; azide-acetyene coupling joining the 'L2' and 'L3' parts of formula 2 results in the triazole moiety as shown.

A representative SN-38 conjugate of an antibody, prepared with a maleimide-containing SN-38-linker derivative, with the bonding to MAb represented as a succinimide, is given (4)

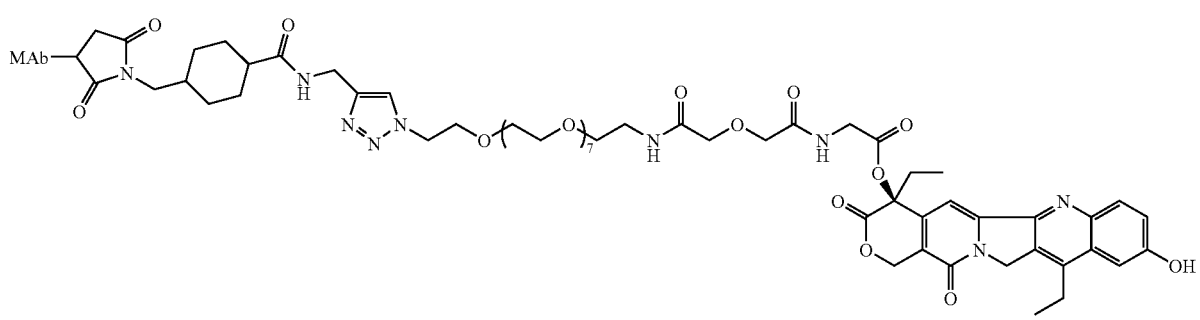

A representative SN-38 conjugate of an antibody, prepared with a maleimide-containing SN-38-linker derivative, with the bonding to MAb represented as a succinimide, is given below. Here, n=0 in the general formula 2; 'L1' contains a cathepsin-B-cleavable dipeptide attached to the collapsible p-aminobenzyl alcohol moiety, and the latter is attached to below. Here, the 20-O-AA ester bonding to SN-38 is glycinate that is attached to L1 portion via a p-aminobenzyl alcohol moiety and a cathepsin-B-cleavable dipeptide; the latter is in turn attached to 'L2' via an amide bond, while 'L2' and 'L3' parts of general formula 2 are coupled via azide-acetylene 'click chemistry' as shown.

(5)

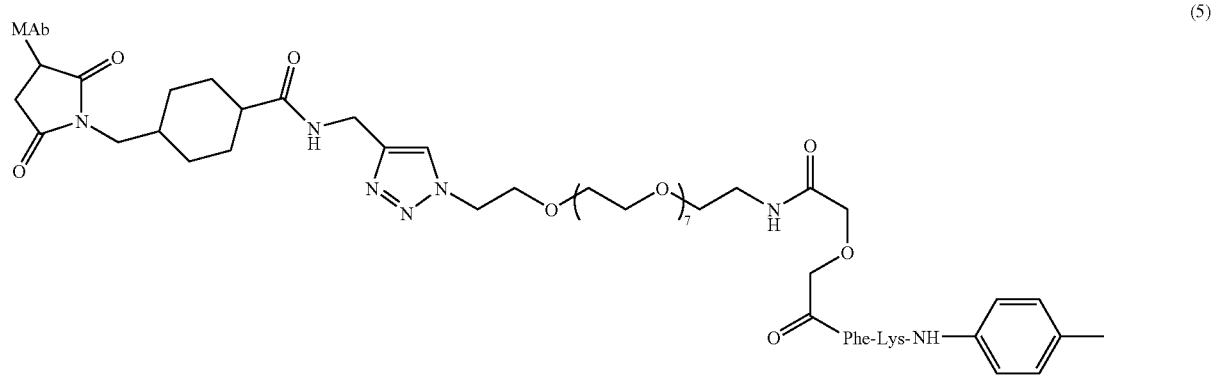

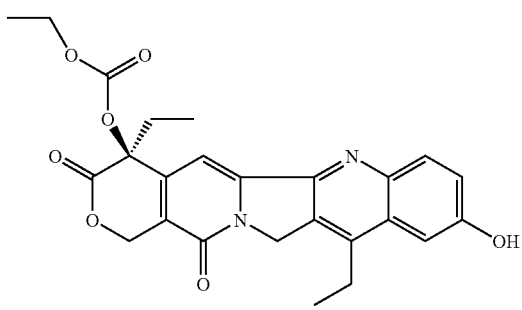

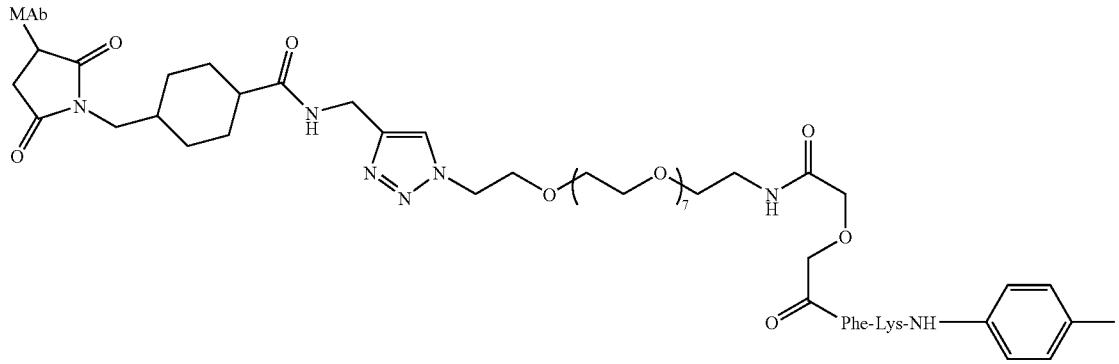

(6)

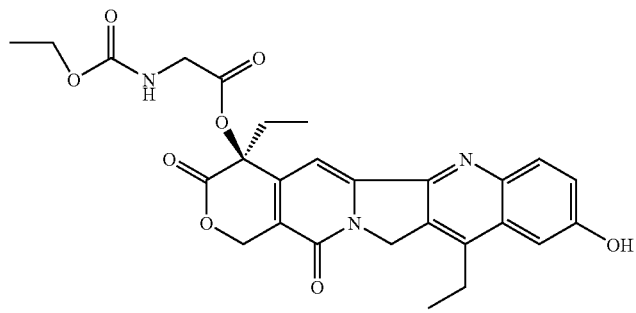

A representative SN-38 conjugate of an antibody, prepared with a maleimide-containing SN-38-linker derivative, with the bonding to MAb represented as a succinimide, is given below. Here, n=0 in the general formula 2; 'L1' contains just the collapsible p-aminobenzyl alcohol moiety, and the latter is attached to SN-38 as a carbonate bonding at the 20 position; azide-acetylene coupling joining the 'L2' and 'L3' parts of formula 2 results in the triazole moiety as shown.

A representative SN-38 conjugate of an antibody, prepared with a maleimide-containing SN-38-linker derivative, with the bonding to MAb represented as a succinimide, is given below. Here, m=0, n=0 in the general formula 2; 'L2' containing azido PEG is attached to SN-38 as a carbonate bonding at the 20 position; azide-acetylene coupling joining the 'L2' and 'L3' parts of formula 2 results in the triazole moiety as shown.

(7)

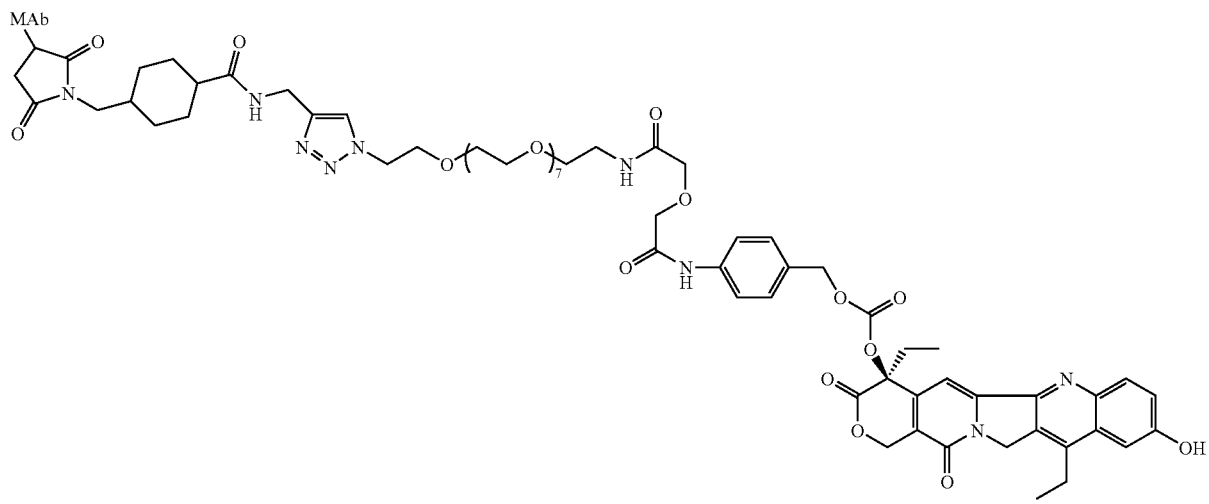

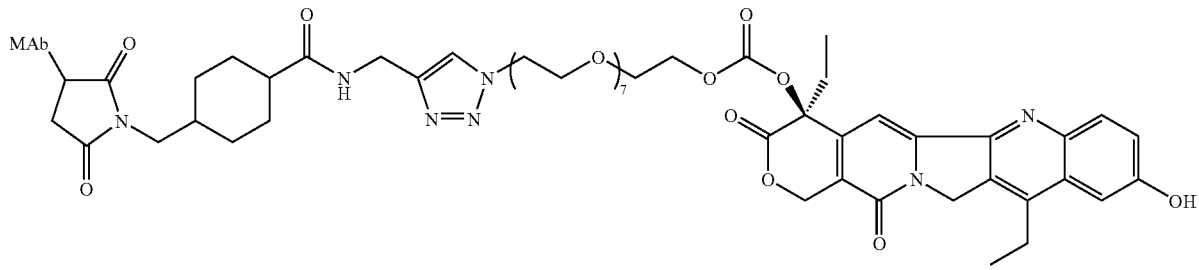

(8)

A representative SN-38 conjugate of an antibody containing multiple drug molecules and a single targeting vector-binding moiety is shown below. 'L3' component of this structure is appended to 2 acetylenic groups, resulting in the attachment of two azide-appended SN-38 molecules. Here, m=0, and the 20-O-AA ester bonding to SN-38 is glycinate; azide-acetylene coupling joining the L2 and L3 parts results in bis-triazole moiety as shown. The bonding to MAb is represented as a succinimide.

A representative SN-38 conjugate of an antibody, prepared with a maleimide-containing SN-38-linker derivative, with the bonding to MAb represented as a succinimide, is given below. Here, the 'AA' is glycinate (i.e. SN-38-20-O-glycinate), which is reacted with an activated acetoacetate. In the L1 portion, the PEG acid is converted to the corresponding hydrazide and attached to SN38-20-O-glycinatoacetoacetate in the form of hydrazone. Azide-acetylene coupling joining the L1 and L2 parts results in the triazole moiety as shown.

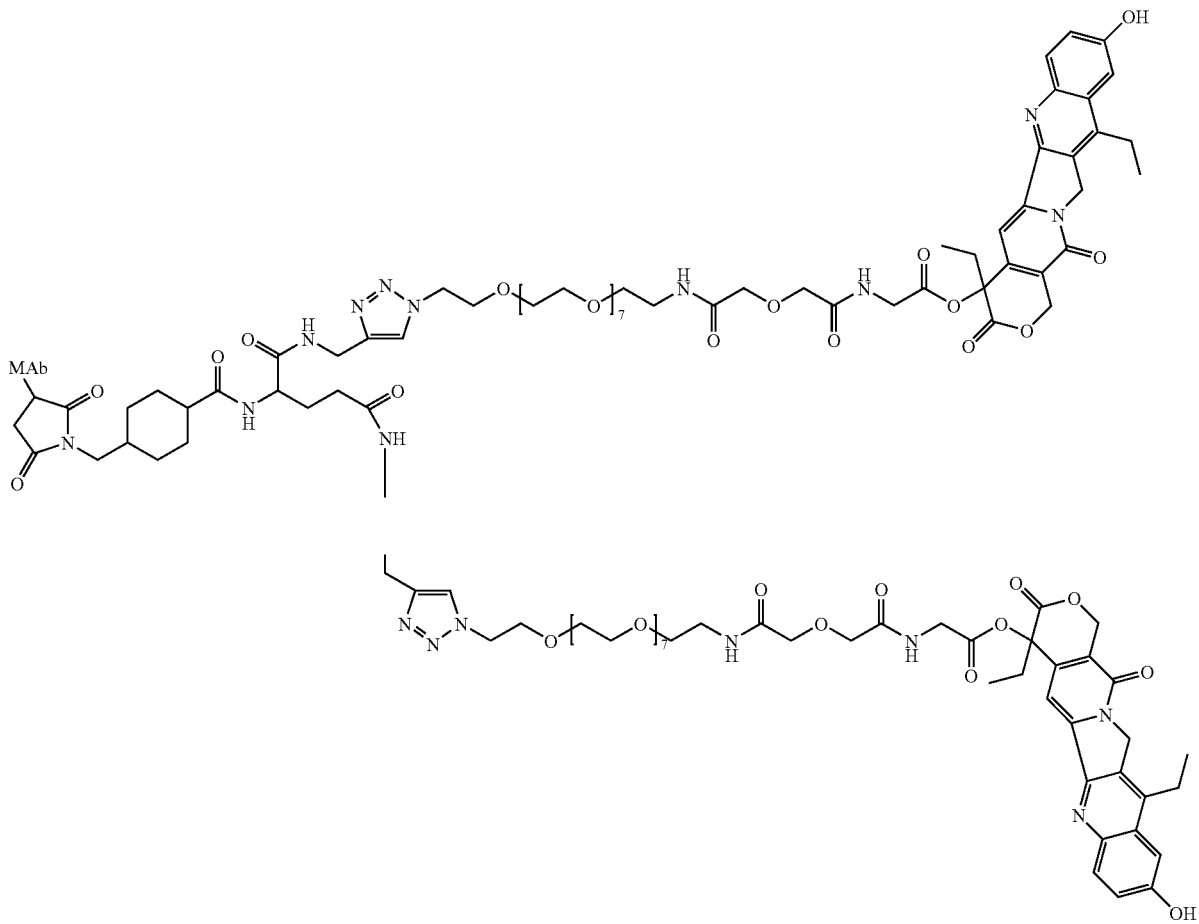

(9)

The cleavable linker ('CL') is the hydrazone moiety in the conjugate, which is cleavable by low pH conditions of certain intracellular compartments.

pared wherein CPT additionally has a 10-hydroxyl group. This process involves, but is not limited to, the protection of the said 10-hydroxyl group as a t-butyloxycarbonyl (BOC)

(10)

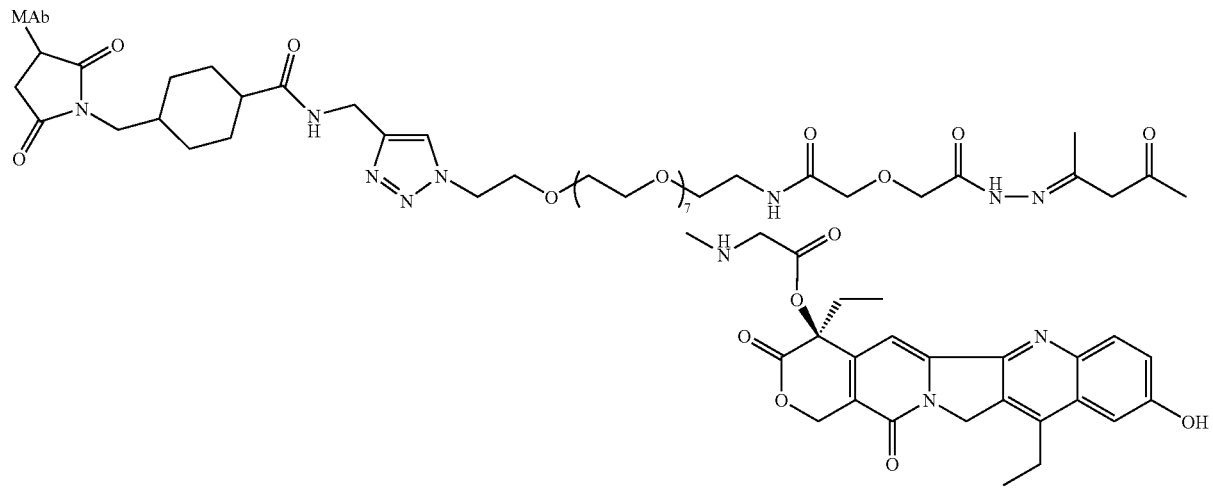

In preferred embodiments, when the bifunctional drug contains thiol-reactive moiety as antibody-binding group, the thiols on the antibody are generated on the lysine groups of the antibody using a thiolating reagent. Methods for introducing thiol groups onto antibodies by modifications of MAb's lysine groups are well known in the art (Wong in *Chemistry of protein conjugation and cross-linking*, CRC Press, Inc., Boca Raton, Fla. (1991), pp 20-22). Alternatively, mild reduction of interchain disulfide bonds on the antibody (Willner et al., *Bioconjugate Chem.* 4:521-527 (1993)) using reducing agents such as dithiothreitol (DTT) can generate 7-to-10 thiols on the antibody; which has the advantage of incorporating multiple CPT moieties upon reaction with [L]-ester-CPT of the general formula given above, in the interchain region of MAb away from antigen-binding region. By this way, the CPT with a thiol-reactive group can be conjugated to MAb either site-specifically on the cysteines generated by disulfide reduction or indirectly on the lysine side chains of MAb derivatized to possess thiol groups.

In a preferred embodiment of the present invention, the preferred chemotherapeutic moiety is selected from the group consisting of CPT, 10-hydroxy camptothecin, SN-38, topotecan, lurtotecan, 9-aminocamptothecin, 9-nitrocamptothecin, and derivatives thereof. In a more preferred embodiment, the chemotherapeutic moiety is SN-38. Preferably, in the conjugates of the preferred embodiments of the present invention, the targeting moiety links to at least one chemotherapeutic moiety; preferably 1 to about 12 chemotherapeutic moieties; most preferably about 6 to about 12 chemotherapeutic moieties.

Furthermore, in a preferred embodiment, the linker component 'L3' comprises a thiol group that reacts with a thiol-reactive residue introduced at one or more lysine side chain amino groups of said targeting moiety. In such cases, the antibody is pre-derivatized with a thiol-reactive group such as a maleimide, vinylsulfone, bromoacetamide, or iodoacetamide by procedures well described in the art.

In the context of these embodiments, a process was surprisingly discovered by which CPT drug-linkers can be prederivative, followed by the preparation of the penultimate intermediate of the drug-linker conjugate. Usually, removal of BOC group requires treatment with strong acid such as trifluoroacetic acid (TFA). Under these conditions, the CPT 20-O-linker carbonate, containing protecting groups to be removed, is also susceptible to cleavage, thereby giving rise to unmodified CPT. In fact, the rationale for using a mildly removable methoxytrityl (MMT) protecting group for the lysine side chain of the linker molecule, as enunciated in the art, was precisely to avoid this possibility (Walker et al., 2002). It was discovered that selective removal of phenolic BOC protecting group is possible by carrying out reactions for short durations, optimally 3-to-5 minutes. Under these conditions, the predominant product was that in which the 'BOC' at 10-hydroxyl position was removed, while the carbonate at '20' position was intact.

An alternative approach involves protecting CPT analogs' 10-hydroxy position with a group other than 'BOC', such that the final product is ready for conjugation to antibodies without a need for deprotecting the 10-OH protecting group. The said 10-hydroxy protecting group, which converts the 10-OH into a phenolic carbonate or a phenolic ester, is readily deprotected by physiological pH conditions or by esterases after in vivo administration of the conjugates. The faster removal of a phenolic carbonate at 10 position vs. tertiary carbonate at 20 position of 10-hydroxycamptothecin under physiological condition has been described by He et al. (He et al., *Bioorganic & Medicinal Chemistry* 12: 4003-4008 (2004)). Structure 11 below shows the SN-38 conjugate of this embodiment, with a 10-hydroxy protecting group on SN-38 shown as 'COR' where R can be a substituted alkyl such as "$N(CH_3)_2$—$(CH_2)_n$—" where n is 2-10 and wherein the terminal amino group is optionally in the form of a quaternary salt for enhanced aqueous solubility, or simple alkyl residue such as "$CH_3$—$(CH_2)_n$—" where n is 0-10, or it can be alkoxy moiety such as "$CH_3$—$(CH_2)_n$—O—" where n is 0-10 or "$N(CH_3)_2$—$(CH_2)_n$—O—" where n is 2-10, or "$R_1O$—$(CH_2$—$CH_2$—$O)_n$—$CH_2$—$CH_2$—O—" where $R_1$ is ethyl or methyl and n is an integer with values of 0-10. These 10-hydroxy derivatives are readily prepared by treatment with the chloroformate of the chosen reagent, if the final derivative is to be a carbonate. Typically, the 10-hydroxy-containing camptothecin such as SN-38 is treated with a molar equivalent of the chloroformate in dimethylformamide using triethylamine as the base. Under these conditions, the 20-OH position is unaffected. For forming 10-O-esters, the acid chloride of the chosen reagent is used.

Multivalent and multispecific or multivalent and monospecific binding proteins may be fusion proteins. In a preferred embodiment, the fusion proteins are assembled by the 'dock and lock (DNL)' technology (Rossi E A, et al., *Proc Natl Acad Sci USA* 2006; 103:6841-6846; U.S. Patent Application Publication Nos. 20060228300; 20070086942 and 20070140966, the text of each of which is incorporated herein by reference in its entirety). The DNL technique is based upon

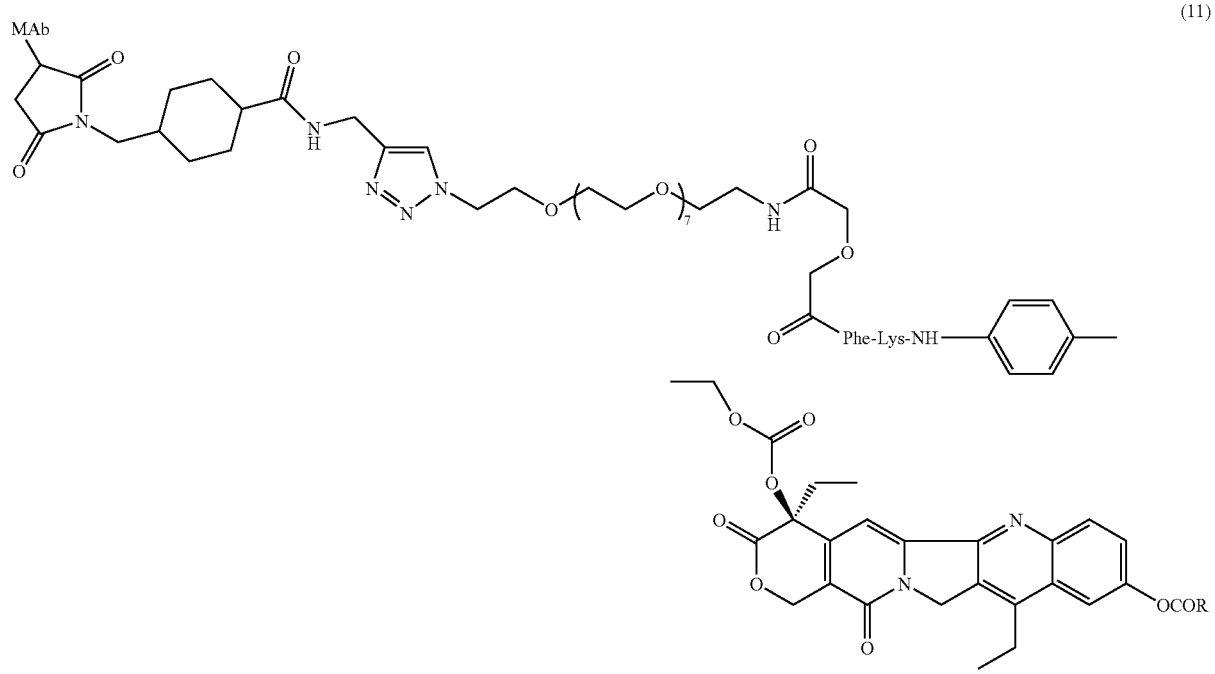

(11)

In one embodiment, the targeting moiety is a monoclonal antibody (MAb). In a further embodiment, the targeting moiety may be a multivalent and/or multispecific MAb. The targeting moiety may be a murine, chimeric, humanized, or human monoclonal antibody, and said antibody may be in intact, fragment (Fab, Fab', F(ab)$_2$, F(ab')$_2$), or sub-fragment (single-chain constructs) form, or of an IgG1, IgG2a, IgG3, IgG4, IgA isotype, or submolecules therefrom.

In a preferred embodiment, the targeting moiety is a monoclonal antibody that is reactive with an antigen or epitope of an antigen expressed on a cancer or malignant cell. The cancer cell is preferably a cell from a hematopoietic tumor, carcinoma, sarcoma, melanoma or a glial tumor. A preferred malignancy to be treated according to the present invention is a malignant solid tumor or hematopoietic neoplasm.

In a preferred embodiment, the intracellularly-cleavable moiety may be cleaved after it is internalized into the cell upon binding by the MAb-drug conjugate to a receptor thereof, and particularly cleaved by esterases and peptidases.

The targeting moiety is preferably an antibody (including fully human, non-human, humanized, or chimeric antibodies) or an antibody fragment (including enzymatically or recombinantly produced fragments) or binding proteins incorporating sequences from antibodies or antibody fragments. The antibodies, fragments, and binding proteins may be multivalent and multispecific or multivalent and monospecific as defined above.

the formation of complexes of naturally occurring binding molecules, for example between the dimerization and docking domain (DDD) regions of the regulatory subunits of cAMP-dependent protein kinase and the anchoring domain (AD) sequence obtained from a wide variety of A-kinase anchoring proteins (AKAPs). The DDD domains spontaneously dimerize and then bind to a single AD sequence. Thus, various effectors may be attached to DDD and AD sequences to form complexes of defined stoichiometry. In the simplest case, the result is a trimer comprising two identical subunits that incorporate a DDD sequence and one subunit that incorporates an AD sequence. However, many variations on such assemblages are possible, including homodimers, homotetramers, heterotetramers and homo or heterohexamers (see US Patent Application Publ. Nos. 20060228357 and 20070140966). Exemplary DDD and AD sequences that may be utilized in the DNL method to form synthetic complexes are disclosed below.

(SEQ ID NO:1)
DDD1 SHIQIPPGLTELLQGYTVEVLRQQPPDLVEFAVEYFTRLREARA (SEQ ID NO:2)
DDD2 CGHIQIPPGLTELLQGYTVEVLRQQPPDLVEFAVEYFTRLREARA

-continued

AD1  QIEYLAKQIVDNAIQQ                           (SEQ ID NO:3)

AD2  CGQIEYLAKQIVDNAIQQAGC                      (SEQ ID NO:4)

In a preferred embodiment of the present invention, antibodies, such as MAbs, are used that recognize or bind to markers or tumor-associated antigens that are expressed at high levels on target cells and that are expressed predominantly or only on diseased cells versus normal tissues, and antibodies that internalize rapidly. Antibodies useful within the scope of the present invention include MAbs with properties as described above (and show distinguishing properties of different levels of internalization into cells and microorganisms), and contemplate the use of, but are not limited to, in cancer, the following MAbs: LL1 (anti-CD74), LL2 and RFB4 (anti-CD22), RS7 (anti-epithelial glycoprotein-1 (EGP-1)), PAM-4 and KC4 (both anti-mucin), MN-14 (anti-carcinoembryonic antigen (CEA, also known as CD66e), MN-3 or MN-15 (NCA or CEACAM6), Mu-9 (anti-colon-specific antigen-p), Immu 31 (an anti-alpha-fetoprotein), TAG-72 (e.g., CC49), Tn, J591 (anti-PSMA (prostate-specific membrane antigen)), G250 (an anti-carbonic anhydrase IX MAb) and L243 (anti-HLA-DR). Such antibodies are known in the art (e.g., U.S. Pat. Nos. 5,686,072; 5,874,540; 6,107,090; 6,183,744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; and U.S. Patent Application Publ. No. 20040185053; 20040202666; 20050271671; 20060193865; 20060210475; 20070087001; each incorporated herein by reference in its entirety.)

Other useful antigens that may be targeted using these conjugates include HER-2/neu, BrE3, CD19, CD20 (e.g., C2B8, hA20, 1F5 MAbs), CD21, CD23, CD37, CD38, CD40, CD45, CD74, CD79, CD80, CD138, alpha-fetoprotein (AFP), VEGF (e.g. AVASTIN®, fibronectin splice variant), ED-B fibronectin (e.g., L19), EGF receptor or ErbB1 (e.g., ERBITUX®), ErbB2, ErbB3, placental growth factor (PlGF), MUC1, MUC2, MUC3, MUC4, MUC5, PSMA, gangliosides, HCG, EGP-2 (e.g., 17-1A), CD37, HLA-DR, CD30, Ia, A3, A33, Ep-CAM, KS-1, Le(y), mesothelin, S100, PSA (prostate-specific antigen), tenascin, folate receptor, Thomas-Friedenreich antigens, tumor necrosis antigens, tumor angiogenesis antigens, Ga 733, IL-2, IL-6, T101, MAGE, insulin-like growth factor (ILGF), macrophage migration-inhibition factor (MIF), the HLA-DR antigen to which L243 binds, CD66 antigens, i.e., CD66a-d or a combination thereof, as well as cancer stem cell antigens, such as CD133 and CD44.

The CD66 antigens consist of five different glycoproteins with similar structures, CD66a-e, encoded by the carcinoembryonic antigen (CEA) gene family members, BCG, CGM6, NCA, CGM1 and CEA, respectively. These CD66 antigens (e.g., CEACAM6) are expressed mainly in granulocytes, normal epithelial cells of the digestive tract and tumor cells of various tissues. Also included as suitable targets for cancers are cancer testis antigens, such as NY-ESO-1 (Theurillat et al., Int. J. Cancer 2007; 120(11):2411-7), as well as CD79a in myeloid leukemia (Kozlov et al., Cancer Genet. Cytogenet. 2005; 163(1):62-7) and also B-cell diseases, and CD79b for non-Hodgkin's lymphoma (Poison et al., Blood 110(2):616-623), all incorporated in their entirety by reference. A number of the aforementioned antigens are disclosed in U.S. Provisional Application Ser. No. 60/426,379, entitled "Use of Multi-specific, Non-covalent Complexes for Targeted Delivery of Therapeutics," filed Nov. 15, 2002, incorporated herein by reference. Cancer stem cells, which are ascribed to be more therapy-resistant precursor malignant cells populations (Gan, J Cell Mol. Med. 2007 Dec. 5 [Epub ahead of print]; Hill and Perris, J. Natl. Cancer Inst. 2007; 99(19:1435-40), have antigens that can be targeted in certain cancer types, such as CD 133 in prostate cancer (Maitland et al., Ernst Schering Found. Sympos. Proc. 2006; 5:155-79), non-small-cell lung cancer (Donnenberg et al., J. Control Release 2007; 122(3):385-91), and glioblastoma (Beier et al., Cancer Res. 2007; 67(9):4010-5), and CD44 in colorectal cancer (Dalerba et al., Proc. Natl. Acad. Sci. USA 2007; 104(24)10158-63), pancreatic cancer (Li et al., Cancer Res. 2007; 67(3):1030-7), and in head and neck squamous cell carcinoma (Prince et al., Proc. Natl. Acad. Sci. USA 2007; 104(3)973-8).

In multiple myeloma therapy, suitable targeting antibodies have been described against, for example, CD38 and CD138 (Stevenson, Mol Med 2006; 12(11-12):345-346; Tassone et al., Blood 2004; 104(12):3688-96), CD74 (Stein et al., ibid.), CS1 (Tai et al., Blood 2007; Oct. 9 (epub ahead of print), and CD40 (Tai et al., 2005; Cancer Res. 65(13):5898-5906).

A recent comprehensive analysis of suitable antigen (Cluster Designation, or CD) targets on hematopoietic malignant cells, as shown by flow cytometry and which can be a guide to selecting suitable antibodies for drug-conjugated immunotherapy, is Craig and Foon, Blood prepublished online Jan. 15, 2008; DOL 10.1182/blood-2007-11-120535, incorporated herein in its entirety by reference.

In another preferred embodiment of the present invention, antibodies are used that internalize rapidly and are then re-expressed, processed and presented on cell surfaces, enabling continual uptake and accretion of circulating conjugate by the cell. An example of a most-preferred antibody/antigen pair is LL1, an anti-CD74 MAb (invariant chain, class II-specific chaperone, Ii) (see, e.g., U.S. Pat. Nos. 6,653,104; 7,312,318; and U.S. Patent Appl. Publ. Nos. 20020187153; 20030220470; 20040185053; 20040202666; 20040219203; 20050271671; 20060014245; 20060193865; 20070207146; each incorporated herein by reference in its entirety). The CD74 antigen is highly expressed on B-cell lymphomas (including multiple myeloma) and leukemias, certain T-cell lymphomas, melanomas, colonic, lung, and renal cancers, glioblastomas, and certain other cancers (Ong et al., Immunology 98:296-302 (1999)), as well as certain autoimmune diseases. A review of the use of CD74 antibodies in cancer is contained in Stein et al., Clin Cancer Res. 2007 Sep. 15; 13(18 Pt 2):5556s-5563s, incorporated herein by reference in its entirety.

The diseases that are preferably treated with anti-CD74 antibodies include, but are not limited to, non-Hodgkin's lymphoma, Hodgkin's disease, melanoma, lung, renal, colonic cancers, glioblastome multiforme, histiocytomas, myeloid leukemias, and multiple myeloma. Continual expression of the CD74 antigen for short periods of time on the surface of target cells, followed by internalization of the antigen, and re-expression of the antigen, enables the targeting LL1 antibody to be internalized along with any chemotherapeutic moiety it carries. This allows a high, and therapeutic, concentration of LL1-chemotherapeutic drug conjugate to be accumulated inside such cells. Internalized LL1-chemotherapeutic drug conjugates are cycled through lysosomes and endosomes, and the chemotherapeutic moiety is released in an active form within the target cells.

In another aspect, the invention relates to a method of treating a subject, comprising administering a therapeutically effective amount of a therapeutic conjugate as described herein to a subject. Diseases that may be treated with the therapeutic conjugates of the preferred embodiments of the present invention include, but are not limited to B-cell malignancies (e.g., non-Hodgkin's lymphoma and chronic lymphocytic leukemia using, for example LL2 MAb; see U.S. Pat. No. 6,183,744), adenocarcinomas of endodermally-derived digestive system epithelia, cancers such as breast cancer and non-small cell lung cancer, and other carcinomas, sarcomas, glial tumors, myeloid leukemias, etc. In particular, antibodies against an antigen, e.g., an oncofetal antigen, produced by or associated with a malignant solid tumor or hematopoietic neoplasm, e.g., a gastrointestinal, lung, breast, prostate, ovarian, testicular, brain or lymphatic tumor, a sarcoma or a melanoma, are advantageously used. Such therapeutics can be given once or repeatedly, depending on the disease state and tolerability of the conjugate, and can also be used optimally in combination with other therapeutic modalities, such as surgery, external radiation, radioimmunotherapy, immunotherapy, chemotherapy, antisense therapy, interference RNA therapy, gene therapy, and the like. Each combination will be adapted to the tumor type, stage, patient condition and prior therapy, and other factors considered by the managing physician.

As used herein, the term "subject" refers to any animal (i.e., vertebrates and invertebrates) including, but not limited to mammals, including humans. The term subject also includes rodents (e.g., mice, rats, and guinea pigs). It is not intended that the term be limited to a particular age or sex. Thus, adult and newborn subjects, as well as fetuses, whether male or female, are encompassed by the term.

In another preferred embodiment, the therapeutic conjugates comprising the Mu-9 MAb of the preferred embodiments of the present invention can be used to treat colorectal, as well as pancreatic and ovarian cancers as disclosed in U.S. Pat. No. 6,962,702 and U.S. application Ser. No. 10/116,116, filed Apr. 5, 2002, each incorporated herein by reference in its entirety and by Gold et al. (*Cancer Res.* 50: 6405 (1990), and references cited therein). In addition, the therapeutic conjugates comprising the PAM-4 MAb of the preferred embodiments of the present invention can be used to treat pancreatic cancer, as disclosed in U.S. Provisional Application Ser. No. 60/388,314, filed Jun. 14, 2002, and U.S. Pat. Nos. 7,238,786 and 7,282,567 each incorporated herein by reference in its entirety.

In another preferred embodiment, the therapeutic conjugates comprising the RS7 MAb (binding to epithelial glycoprotein-1 [EGP-1] antigen) of the preferred embodiments can be used to treat carcinomas such as carcinomas of the lung, stomach, urinary bladder, breast, ovary, uterus, and prostate, as disclosed in U.S. Provisional Application Ser. No. 60/360, 229, filed Mar. 1, 2002, and U.S. Pat. No. 7,238,785, incorporated herein by reference in its entirety and by Stein et al. (*Cancer Res.* 50: 1330 (1990) and *Antibody Immunoconj. Radiopharm.* 4: 703 (1991)).

In another preferred embodiment, the therapeutic conjugates comprising the anti-AFP MAb of the preferred embodiments can be used to treat hepatocellular carcinoma, germ cell tumors, and other AFP-producing tumors using humanized, chimeric and human antibody forms, as disclosed in U.S. Provisional Application Ser. No. 60/399,707, filed Aug. 1, 2002, and U.S. Pat. No. 7,300,655, incorporated herein by reference in its entirety.

In another preferred embodiment, the therapeutic conjugates comprising anti-tenascin antibodies can be used to treat hematopoietic and solid tumors and conjugates comprising antibodies to tenascin can be used to treat solid tumors, preferably brain cancers like glioblastomas.

In a preferred embodiment, the antibodies that are used in the treatment of human disease are human or humanized (CDR-grafted) versions of antibodies; although murine and chimeric versions of antibodies can be used. Same species IgG molecules as delivery agents are mostly preferred to minimize immune responses. This is particularly important when considering repeat treatments. For humans, a human or humanized IgG antibody is less likely to generate an anti-IgG immune response from patients. Antibodies such as hLL1 and hLL2 rapidly internalize after binding to internalizing antigen on target cells, which means that the chemotherapeutic drug being carried is rapidly internalized into cells as well. However, antibodies that have slower rates of internalization can also be used to effect selective therapy with this invention.

In another preferred embodiment, the therapeutic conjugates of the preferred embodiments can be used against pathogens, since antibodies against pathogens are known. For example, antibodies and antibody fragments which specifically bind markers produced by or associated with infectious lesions, including viral, bacterial, fungal and parasitic infections, for example caused by pathogens such as bacteria, rickettsia, mycoplasma, protozoa, fungi, and viruses, and antigens and products associated with such microorganisms have been disclosed, inter alia, in Hansen et al., U.S. Pat. No. 3,927,193 and Goldenberg U.S. Pat. Nos. 4,331,647, 4,348, 376, 4,361,544, 4,468,457, 4,444,744, 4,818,709 and 4,624, 846, each incorporated herein by reference, and in Reichert and Dewitz, cited above. In a preferred embodiment, the pathogens are selected from the group consisting of HIV virus causing AIDS, *Mycobacterium tuberculosis*, *Streptococcus agalactiae*, methicillin-resistant *Staphylococcus aureus*, *Legionella pneumophilia*, *Streptococcus pyogenes*, *Escherichia coli*, *Neisseria gonorrhosae*, *Neisseria meningitidis*, *Pneumococcus*, *Cryptococcus neoformans*, *Histoplasma capsulatum*, *Hemophilis influenzae* B, *Treponema pallidum*, Lyme disease spirochetes, *Pseudomonas aeruginosa*, *Mycobacterium leprae*, *Brucella abortus*, rabies virus, influenza virus, cytomegalovirus, herpes simplex virus I, herpes simplex virus II, human serum parvo-like virus, respiratory syncytial virus, varicella-zoster virus, hepatitis B virus, hepatitis C virus, measles virus, adenovirus, human T-cell leukemia viruses, Epstein-Barr virus, murine leukemia virus, mumps virus, vesicular stomatitis virus, sindbis virus, lymphocytic choriomeningitis virus, wart virus, blue tongue virus, Sendai virus, feline leukemia virus, reovirus, polio virus, simian virus 40, mouse mammary tumor virus, dengue virus, rubella virus, West Nile virus, *Plasmodium falciparum*, *Plasmodium vivax*, *Toxoplasma gondii*, *Trypanosoma rangeli*, *Trypanosoma cruzi*, *Trypanosoma rhodesiensei*, *Trypanosoma brucei*, *Schistosoma mansoni*, *Schistosoma japanicum*, *Babesia bovis*, *Elmeria tenella*, *Onchocerca volvulus*, *Leishmania tropica*, *Trichinella spiralis*, *Theileria parva*, *Taenia hydatigena*, *Taenia ovis*, *Taenia saginata*, *Echinococcus granulosus*, *Mesocestoides corti*, *Mycoplasma arthritidis*, *M. hyorhinis*, *M. orale*, *M. arginini*, *Acholeplasma laidlawii*, *M. salivarium* and *M. pneumoniae*, as disclosed in U.S. Pat. No. 6,440,416, incorporated herein by reference.

In a more preferred embodiment, drug conjugates of the present invention comprising anti-gp120 and other such anti-HIV antibodies can be used as therapeutics for HIV in AIDS patients; and drug conjugates of antibodies to *Mycobacterium tuberculosis* are suitable as therapeutics for drug-refractive tuberculosis. Fusion proteins of anti-gp120 MAb (anti HIV MAb) and a toxin, such as *Pseudomonas* exotoxin, have been examined for antiviral properties (Van Oigen et al., *J Drug Target*, 5:75-91, 1998). Attempts at treating HIV infection in AIDS patients failed, possibly due to insufficient efficacy or unacceptable host toxicity. The drug conjugates of the present invention advantageously lack such toxic side effects of protein toxins, and are therefore advantageously used in treating HIV infection in AIDS patients. These drug conjugates can be given alone or in combination with other antibiotics or therapeutic agents that are effective in such patients when given alone. Candidate anti-HIV antibodies include the anti-envelope antibody described by Johansson et al. (AIDS. 2006 Oct. 3; 20(15):1911-5), as well as the anti-HIV antibodies described and sold by Polymun (Vienna, Austria), also described in U.S. Pat. No. 5,831,034, U.S. Pat. No. 5,911,989, and Vcelar et al., AIDS 2007; 21(16):2161-2170 and Joos et al., Antimicrob. Agens Chemother. 2006; 50(5):1773-9, all incorporated herein in their entirety by reference. A preferred targeting agent for HIV is various combinations of these antibodies in order to overcome resistance.

In another preferred embodiment, diseases that may be treated using the therapeutic conjugates of the preferred embodiments of the present invention include, but are not limited to immune dysregulation disease and related autoimmune diseases, including Class III autoimmune diseases such as immune-mediated thrombocytopenias, such as acute idiopathic thrombocytopenic purpura and chronic idiopathic thrombocytopenic purpura, dermatomyositis, Sjögren's syndrome, multiple sclerosis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, sarcoidosis, ulcerative colitis, erythema multiforme, IgA nephropathy, polyarteritis nodosa, ankylosing spondylitis, Goodpasture's syndrome, thromboangitis ubiterans, Sjögren's syndrome, primary biliary cirrhosis, Hashimoto's thyroiditis, thyrotoxicosis, scleroderma, chronic active hepatitis, rheumatoid arthritis, polymyositis/dermatomyositis, polychondritis, pamphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis, and also juvenile diabetes, as disclosed in U.S. Provisional Application Ser. No. 60/360,259, filed Mar. 1, 2002. Typical antibodies useful in these diseases include, but are not limited to, those reactive with HLA-DR antigens, B-cell and plasma-cell antigens (e.g., CD19, CD20, CD21, CD22, CD23, CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, B7, MUC1, Ia, HM1.24, and HLA-DR), IL-6, IL-17. Since many of these autoimmune diseases are affected by autoantibodies made by aberrant B-cell populations, depletion of these B-cells by therapeutic conjugates involving such antibodies-therapeutic agent conjugates described herein is a preferred method of autoimmune disease therapy, especially when B-cell antibodies are combined, in certain circumstances, with HLA-DR antibodies and/or T-cell antibodies (including those which target IL-2 as an antigen, such as anti-TAC antibody). In a preferred embodiment, the anti-B-cell, anti-T-cell, or anti-macrophage or other such antibodies of use in the treatment of patients with autoimmune diseases also can be conjugated to result in more effective therapeutics to control the host responses involved in said autoimmune diseases, and can be given alone or in combination with other therapeutic agents, such as TNF inhibitors or TNF antibodies, unconjugated B- or T-cell antibodies, and the like.

In a preferred embodiment of this invention, a more effective incorporation into cells and pathogens can be accomplished by using multivalent, multispecific or multivalent, monospecific antibodies. Multivalent means the use of several binding arms against the same or different antigen or epitope expressed on the cells, whereas multispecific antibodies involve the use of multiple binding arms to target at least two different antigens or epitopes contained on the targeted cell or pathogen. Examples of such bivalent and bispecific antibodies are found in U.S. patent applications 60/399,707, filed Aug. 1, 2002; 60/360,229, filed Mar. 1, 2002; 60/388, 314, filed Jun. 14, 2002; and 10/116,116, filed Apr. 5, 2002, each of which is incorporated herein by reference in its entirety. These multivalent or multispecific antibodies are particularly preferred in the targeting of cancers and infectious organisms (pathogens), which express multiple antigen targets and even multiple epitopes of the same antigen target, but which often evade antibody targeting and sufficient binding for immunotherapy because of insufficient expression or availability of a single antigen target on the cell or pathogen. By targeting multiple antigens or epitopes, said antibodies show a higher binding and residence time on the target, thus affording a higher saturation with the drug being targeted in this invention.

In another preferred embodiment, a therapeutic agent used in combination with the camptothecin conjugate of this invention may comprise one or more isotopes, such as $^{212}$Bi, $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94}$Tc, $^{94m}$Tc, $^{99m}$Tc or $^{111}$In. Non-radioactive metals, such as manganese, iron and gadolinium, are useful for nuclear imaging or MRI, when used along with the stably tethered structures and carriers described herein, or as direct therapeutics (e.g., when a beta- alpha- or Auger-emitting radionuclide is used), all of which are contemplated as useful herein. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates, such as macrocyclic polyethers for complexing $^{223}$Ra, may be used. Therapeutic agents for use in combination with the camptothecin conjugate of this invention also include, for example, chemotherapeutic drugs such as vinca alkaloids, anthracyclines, epidophyllotoxins, taxanes, antimetabolites, alkylating agents, antibiotics, Cox-2 inhibitors, antimitotics, antiangiogenic and proapoptotic agents, particularly doxorubicin, methotrexate, taxol, other camptothecins, and others from these and other classes of anticancer agents, and the like. Other cancer chemotherapeutic drugs include nitrogen mustards, alkyl sulfonates, nitrosoureas, triazenes, folic acid analogs, pyrimidine analogs, purine analogs, platinum coordination complexes, hormones, and the like. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art.

Another class of therapeutic agents consists of radionuclides that emit α-particles (such as $^{212}$Pb, $^{212}$Bi, $^{213}$Bi, $^{211}$At, $^{223}$Ra, $^{225}$Ac), β-particles (such as $^{32}$P, $^{33}$P, $^{47}$Sc, $^{67}$Cu, $^{67}$Ga, $^{89}$Sr, $^{90}$Y, $^{111}$Ag, $^{125}$I, $^{131}$I, $^{142}$Pr, $^{153}$Sm, $^{161}$Tb, $^{166}$Ho, $^{166}$Dy, $^{177}$Lu, $^{186}$Re, $^{188}$Re, $^{189}$Re), or Auger electrons (such as $^{111}$In, $^{125}$I, $^{67}$Ga, $^{191}$Os, $^{193m}$Pt, $^{195m}$Pt, $^{195m}$Hg). Alternatively therapeutic agents may comprise a radioisotope useful for diagnostic imaging. Suitable radioisotopes may include those in the energy range of 60 to 4,000 KeV, or more specifically, $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94m}$Tc, $^{94}$Tc, $^{99m}$Tc, $^{45}$Ti, $^{111}$In, $^{123}$I, $^{124}$I, $^{125}$I, $^{131}$I, $^{154-158}$Gd, $^{177}$Lu, $^{32}$P, $^{188}$Re, and the like, or a combination thereof. See, e.g., U.S. patent application entitled "Labeling Targeting Agents with Gallium-68" (Griffiths, G. L. and W. J. McBride, W. J, U.S. Provisional Application No. 60/342,104) which discloses positron emitters, such as $^{18}$F, $^{68}$Ga, $^{94m}$Tc, and the like, for imaging purposes; incorporated entirely by reference. Detection can be achieved, for example, by single photon emission computed tomography (SPECT), or positron emission tomography (PET). The application also may be for intraoperative diagnosis to identify occult neoplastic tumors. Imaging therapeutic agents may include one or more image enhancing agents, which may include complexes of metals selected from the group consisting of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III).

In still other embodiments, a therapeutic agent may comprise one or more radioactive isotopes useful for killing neoplastic or other rapidly dividing cells, which include β-emitters (such as $^{32}$P, $^{33}$P, $^{47}$Sc, $^{67}$Cu, $^{67}$Ga, $^{89}$Sr, $^{90}$Y, $^{111}$Ag, $^{125}$I, $^{131}$I, $^{142}$Pr, $^{153}$Sm, $^{161}$Tb, $^{166}$Ho, $^{166}$Dy, $^{177}$Lu, $^{186}$Re, $^{188}$Re, $^{189}$Re), Auger electron emitters (such as $^{111}$In, $^{125}$I, $^{67}$Ga, $^{191}$Os, $^{193m}$Pt, $^{195m}$Pt, $^{195m}$Hg), α-emitters (such as $^{212}$Pb, $^{212}$Bi, $^{213}$Bi, $^{211}$At, $^{223}$Ra, $^{225}$Ac), or a combination thereof.

Therapeutic agents to be used in concert with the camptothecin conjugates also may be toxins conjugated to targeting moieties. Toxins that may be used in this regard include ricin, abrin, ribonuclease (RNase), DNase I, Staphylococcal enterotoxin-A, pokeweed antiviral protein, gelonin, diphtherin toxin, *Pseudomonas* exotoxin, and *Pseudomonas* endotoxin. (See, e.g., Pastan. et al., Cell (1986), 47:641, and Sharkey and Goldenberg, C A Cancer J Clin. 2006 July-August; 56(4):226-43.) Additional toxins suitable for use herein are known to those of skill in the art and are disclosed in U.S. Pat. No. 6,077,499, which is incorporated herein by reference in its entirety.

In various embodiments, a conjugate as disclosed herein may be part of a composite, multispecific antibody. Such antibodies may contain two or more different antigen binding sites, with differing specificities. The multispecific composite may bind to different epitopes of the same antigen, or alternatively may bind to two different antigens. Some of the more preferred target combinations include the following. This is a list of examples of preferred combinations, but is not intended to be exhaustive.

TABLE 1

Some Examples of multispecific antibodies.

| First target | Second target |
| --- | --- |
| MIF | A second proinflammatory effector cytokine, especially HMGB-1, TNF-α, IL-1, or IL-6 |
| MIF | Proinflammatory effector chemokine, especially MCP-1, RANTES, MIP-1A, or MIP-1B |
| MIF | Proinflammatory effector receptor, especially IL-6R IL-13R, and IL-15R |
| MIF | Coagulation factor, especially TF or thrombin |
| MIF | Complement factor, especially C3, C5, C3a, or C5a |
| MIF | Complement regulatory protein, especially CD46, CD55, CD59, and mCRP |
| MIF | Cancer associated antigen or receptor |
| HMGB-1 | A second proinflammatory effector cytokine, especially MIF, TNF-α, IL-1, or IL-6 |
| HMGB-1 | Proinflammatory effector chemokine, especially MCP-1, RANTES, MIP-1A, or MIP-1B |
| HMGB-1 | Proinflammatory effector receptor especially MCP-1, RANTES, MIP-1A, or MIP-1B |
| HMGB-1 | Coagulation factor, especially TF or thrombin |
| HMGB-1 | Complement factor, especially C3, C5, C3a, or C5a |
| HMGB-1 | Complement regulatory protein, especially CD46, CD55, CD59, and mCRP |
| HMGB-1 | Cancer associated antigen or receptor |
| TNF-α | A second proinflammatory effector cytokine, especially MIF, HMGB-1, TNF-α, IL-1, or IL-6 |
| TNF-α | Proinflammatory effector chemokine, especially MCP-1, RANTES, MIP-1A, or MIP-1B |
| TNF-α | Proinflammatory effector receptor, especially IL-6R IL-13R, and IL-15R |
| TNF-α | Coagulation factor, especially TF or thrombin |
| TNF-α | Complement factor, especially C3, C5, C3a, or C5a |
| TNF-α | Complement regulatory protein, especially CD46, CD55, CD59, and mCRP |
| TNF-α | Cancer associated antigen or receptor |
| LPS | Proinflammatory effector cytokine, especially MIF, HMGB-1, TNF-α, IL-1, or IL-6 |
| LPS | Proinflammatory effector chemokine, especially MCP-1, RANTES, MIP-1A, or MIP-1B |
| LPS | Proinflammatory effector receptor, especially IL-6R IL-13R, and IL-15R |
| LPS | Coagulation factor, especially TF or thrombin |
| LPS | Complement factor, especially C3, C5, C3a, or C5a |
| LPS | Complement regulatory protein, especially CD46, CD55, CD59, and mCRP |

TABLE 1-continued

Some Examples of multispecific antibodies.

| First target | Second target |
| --- | --- |
| TF or thrombin | Proinflammatory effector cytokine, especially MIF, HMGB-1, TNF-α, IL-1, or IL-6 |
| TF or thrombin | Proinflammatory effector chemokine, especially MCP-1, RANTES, MIP-1A, or MIP-1B |
| TF or thrombin | Proinflammatory effector receptor, especially IL-6R, IL-13R, and IL-15R |
| TF or thrombin | Complement factor, especially C3, C5, C3a, or C5a |
| TF or thrombin | Complement regulatory protein, especially CD46, CD55, CD59, and mCRP |
| TF or thrombin | Cancer associated antigen or receptor |

Still other combinations, such as are preferred for cancer therapies, include CD20+CD22 antibodies, CD74+CD20 antibodies, CD74+CD22 antibodies, CEACAM5 (CEA)+ CEACAM6 (NCA) antibodies, insulin-like growth factor (ILGF)+CEACAM5 antibodies, EGP-1 (e.g., RS-7)+ILGF antibodies, CEACAM5+EGFR antibodies. Such antibodies need not only be used in combination, but can be combined as fusion proteins of various forms, such as IgG, Fab, scFv, and the like, as described in U.S. Pat. Nos. 6,083,477; 6,183,744 and 6,962,702 and U.S. Patent Application Publication Nos. 20030124058; 20030219433; 20040001825; 20040202666; 20040219156; 20040219203; 20040235065; 20050002945; 20050014207; 20050025709; 20050079184; 20050169926; 20050175582; 20050249738; 20060014245 and 20060034759, each incorporated herein by reference in their entirety.

In certain embodiments, the binding moieties described herein may comprise one or more avimer sequences. Avimers are a class of binding proteins somewhat similar to antibodies in their affinities and specificities for various target molecules. They were developed from human extracellular receptor domains by in vitro exon shuffling and phage display. Methods of construction and use of avimers are discussed in more detail below.

Production of Antibody Fragments

Methods of monoclonal antibody production are well known in the art and any such known method may be used to produce antibodies of use in the claimed methods and compositions. Some embodiments of the claimed methods and/or compositions may concern antibody fragments. Such antibody fragments may be obtained by pepsin or papain digestion of whole antibodies by conventional methods. For example, antibody fragments may be produced by enzymatic cleavage of antibodies with pepsin to provide a 5S fragment denoted F(ab')$_2$. This fragment may be further cleaved using a thiol reducing agent and, optionally, a blocking group for the sulfhydryl groups resulting from cleavage of disulfide linkages, to produce 3.5S Fab' monovalent fragments. Alternatively, an enzymatic cleavage using pepsin produces two monovalent Fab fragments and an Fc fragment. Exemplary methods for producing antibody fragments are disclosed in U.S. Pat. No. 4,036,945; U.S. Pat. No. 4,331,647; Nisonoff et al., 1960, Arch. Biochem. Biophys., 89:230; Porter, 1959, Biochem. J., 73:119; Edelman et al., 1967, METHODS IN ENZYMOLOGY, page 422 (Academic Press), and Coligan et al. (eds.), 1991, CURRENT PROTOCOLS IN IMMUNOLOGY, (John Wiley & Sons).

Other methods of cleaving antibodies, such as separation of heavy chains to form monovalent light-heavy chain fragments, further cleavage of fragments or other enzymatic, chemical or genetic techniques also may be used, so long as the fragments bind to the antigen that is recognized by the intact antibody. For example, Fv fragments comprise an association of $V_H$ and $V_L$ chains. This association can be noncovalent, as described in Inbar et al., 1972, Proc. Nat'l. Acad. Sci. USA, 69:2659. Alternatively, the variable chains may be linked by an intermolecular disulfide bond or cross-linked by chemicals such as glutaraldehyde. See Sandhu, 1992, Crit. Rev. Biotech., 12:437.

Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains, connected by an oligonucleotides linker sequence. The structural gene is inserted into an expression vector that is subsequently introduced into a host cell, such as *E. coli*. The recombinant host cells synthesize a single polypeptide chain with a linker peptide bridging the two V domains. Methods for producing sFvs are well-known in the art. See Whitlow et al., 1991, Methods: A Companion to Methods in Enzymology 2:97; Bird et al., 1988, Science, 242:423; U.S. Pat. No. 4,946,778; Pack et al., 1993, Bio/Technology, 11:1271, and Sandhu, 1992, Crit. Rev. Biotech., 12:437.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See Larrick et al., 1991, Methods: A Companion to Methods in Enzymology 2:106; Ritter et al. (eds.), 1995, MONOCLONAL ANTIBODIES: PRODUCTION, ENGINEERING AND CLINICAL APPLICATION, pages 166-179 (Cambridge University Press); Birch et al., (eds.), 1995, MONOCLONAL ANTIBODIES: PRINCIPLES AND APPLICATIONS, pages 137-185 (Wiley-Liss, Inc.)

Chimeric and Humanized Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. Methods for constructing chimeric antibodies are well known in the art (e.g., Leung et al., 1994, Hybridoma 13:469).

A chimeric monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. To preserve the stability and antigen specificity of the humanized monoclonal, one or more human FR residues may be replaced by the mouse counterpart residues. Humanized monoclonal antibodies may be used for therapeutic treatment of subjects. The affinity of humanized antibodies for a target may also be increased by selected modification of the CDR sequences (WO0029584A1). Techniques for production of humanized monoclonal antibodies are well known in the art. (See, e.g., Jones et al., 1986, Nature, 321:522; Riechmann et al., Nature, 1988, 332:323; Verhoeyen et al., 1988, Science, 239:1534; Carter et al., 1992, Proc. Nat'l Acad. Sci. USA, 89:4285; Sandhu, Crit. Rev. Biotech., 1992, 12:437; Tempest et al., 1991, Biotechnology 9:266; Singer et al., J. Immun., 1993, 150:2844.)

Other embodiments may concern non-human primate antibodies. General techniques for raising therapeutically useful antibodies in baboons may be found, for example, in Goldenberg et al., WO 91/11465 (1991), and in Losman et al., Int. J. Cancer 46: 310 (1990). In another embodiment, an antibody may be a human monoclonal antibody. Such antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int. Immun. 6:579 (1994).

Human Antibodies

Methods for producing fully human antibodies using either combinatorial approaches or transgenic animals transformed with human immunoglobulin loci are known in the art (e.g., Mancini et al., 2004, New Microbiol. 27:315-28; Conrad and Scheller, 2005, Comb. Chem. High Throughput Screen. 8:117-26; Brekke and Loset, 2003, Curr. Opin. Phamacol. 3:544-50; each incorporated herein by reference). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, Genet. Mol. Res. 4:126-40, incorporated herein by reference). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.) Recombinant Fab were cloned from the µ, γ and κ chain antibody repertoires and inserted into a phage display library (Id.) RNAs were converted to cDNAs and used to make Fab cDNA libraries using specific primers against the heavy and light chain immunoglobulin sequences (Marks et al., 1991, J. Mol. Biol. 222:581-97, incorporated herein by reference). Library construction was performed according to Andris-Widhopf et al. (2000, In: *Phage Display Laboratory Manual*, Barbas et al. (eds), 1$^{st}$ edition, Cold Spring Harbor Laboratory Press, Cold Spring Harbor, N.Y. pp. 9.1 to 9.22, incorporated herein by reference). The final Fab fragments were digested with restriction endonucleases and inserted into the bacteriophage genome to make the phage display library. Such libraries may be screened by standard phage display methods. The skilled artisan will realize that this technique is exemplary only and any known method for making and screening human antibodies or antibody fragments by phage display may be utilized.

In another alternative, transgenic animals that have been genetically engineered to produce human antibodies may be used to generate antibodies against essentially any immunogenic target, using standard immunization protocols as discussed above. A non-limiting example of such a system is the XenoMouse® (e.g., Green et al., 1999, *J. Immunol. Methods* 231:11-23, incorporated herein by reference) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Ig kappa loci, including the majority of the variable region sequences, along accessory genes and regulatory sequences. The human variable region repertoire may be used to generate antibody producing B cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Such human antibodies may be coupled to other molecules by chemical cross-linking or other known methodologies. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

Avimers

In certain embodiments, the precursors, monomers and/or complexes described herein may comprise one or more er sequences. Avimers are a class of binding proteins somewhat similar to antibodies in their affinities and specifities for various target molecules. They were developed from human extracellular receptor domains by in vitro exon shuffling and phage display. (Silverman et al., 2005, Nat. Biotechnol. 23:1493-94; Silverman et al., 2006, Nat. Biotechnol. 24:220.) The resulting multidomain proteins may comprise multiple independent binding domains, that may exhibit improved affinity (in some cases sub-nanomolar) and specificity compared with single-epitope binding proteins. (Id.) In various embodiments, avimers may be attached to, for example, DDD and/or AD sequences for use in the claimed methods and compositions. Additional details concerning methods of construction and use of avimers are disclosed, for example, in U.S. Patent Application Publication Nos. 20040175756, 20050048512, 20050053973, 20050089932 and 20050221384, the Examples section of each of which is incorporated herein by reference.

Phage Display

Certain embodiments of the claimed compositions and/or methods may concern binding peptides and/or peptide mimetics of various target molecules, cells or tissues. Binding peptides may be identified by any method known in the art, including but not limiting to the phage display technique. Various methods of phage display and techniques for producing diverse populations of peptides are well known in the art. For example, U.S. Pat. Nos. 5,223,409; 5,622,699 and 6,068,829, each of which is incorporated herein by reference, disclose methods for preparing a phage library. The phage display technique involves genetically manipulating bacteriophage so that small peptides can be expressed on their surface (Smith and Scott, 1985, Science 228:1315-1317; Smith and Scott, 1993, Meth. Enzymol. 21:228-257).

The past decade has seen considerable progress in the construction of phage-displayed peptide libraries and in the development of screening methods in which the libraries are used to isolate peptide ligands. For example, the use of peptide libraries has made it possible to characterize interacting sites and receptor-ligand binding motifs within many proteins, such as antibodies involved in inflammatory reactions or integrins that mediate cellular adherence. This method has also been used to identify novel peptide ligands that may serve as leads to the development of peptidomimetic drugs or imaging agents (Arap et al., 1998a, Science 279:377-380). In addition to peptides, larger protein domains such as single-chain antibodies may also be displayed on the surface of phage particles (Arap et al., 1998a).

Targeting amino acid sequences selective for a given organ, tissue, cell type or target molecule may be isolated by panning (Pasqualini and Ruoslahti, 1996, Nature 380:364-366; Pasqualini, 1999, The Quart. J. Nucl. Med. 43:159-162). In brief, a library of phage containing putative targeting peptides is administered to an intact organism or to isolated organs, tissues, cell types or target molecules and samples containing bound phage are collected. Phage that bind to a target may be eluted from a target organ, tissue, cell type or target molecule and then amplified by growing them in host bacteria.

In certain embodiments, the phage may be propagated in host bacteria between rounds of panning. Rather than being lysed by the phage, the bacteria may instead secrete multiple copies of phage that display a particular insert. If desired, the amplified phage may be exposed to the target organs, tissues, cell types or target molecule again and collected for additional rounds of panning. Multiple rounds of panning may be performed until a population of selective or specific binders is obtained. The amino acid sequence of the peptides may be determined by sequencing the DNA corresponding to the targeting peptide insert in the phage genome. The identified targeting peptide may then be produced as a synthetic peptide by standard protein chemistry techniques (Arap et al., 1998a, Smith et al., 1985).

In some embodiments, a subtraction protocol may be used to further reduce background phage binding. The purpose of subtraction is to remove phage from the library that bind to targets other than the target of interest. In alternative embodiments, the phage library may be prescreened against a control cell, tissue or organ. For example, tumor-binding peptides may be identified after prescreening a library against a control normal cell line. After subtraction the library may be screened against the molecule, cell, tissue or organ of interest. Other methods of subtraction protocols are known and may be used in the practice of the claimed methods, for example as disclosed in U.S. Pat. Nos. 5,840,841, 5,705,610, 5,670,312 and 5,492,807, incorporated herein by reference.

Aptamers

In certain embodiments, a targeting moiety of use may be an aptamer. Methods of constructing and determining the binding characteristics of aptamers are well known in the art. For example, such techniques are described in U.S. Pat. Nos. 5,582,981, 5,595,877 and 5,637,459, each incorporated herein by reference. Methods for preparation and screening of aptamers that bind to particular targets of interest are well known, for example U.S. Pat. No. 5,475,096 and U.S. Pat. No. 5,270,163, each incorporated herein by reference.

Aptamers may be prepared by any known method, including synthetic, recombinant, and purification methods, and may be used alone or in combination with other ligands specific for the same target. In general, a minimum of approximately 3 nucleotides, preferably at least 5 nucleotides, are necessary to effect specific binding. Aptamers of sequences shorter than 10 bases may be feasible, although aptamers of 10, 20, 30 or 40 nucleotides may be preferred.

Aptamers need to contain the sequence that confers binding specificity, but may be extended with flanking regions and otherwise derivatized. In preferred embodiments, the binding sequences of aptamers may be flanked by primer-binding sequences, facilitating the amplification of the aptamers by PCR or other amplification techniques.

Aptamers may be isolated, sequenced, and/or amplified or synthesized as conventional DNA or RNA molecules. Alternatively, aptamers of interest may comprise modified oligomers. Any of the hydroxyl groups ordinarily present in aptamers may be replaced by phosphonate groups, phosphate groups, protected by a standard protecting group, or activated to prepare additional linkages to other nucleotides, or may be conjugated to solid supports. One or more phosphodiester linkages may be replaced by alternative linking groups, such as $P(O)O$ replaced by $P(O)S$, $P(O)NR_2$, $P(O)R$, $P(O)OR'$, $CO$, or $CNR_2$, wherein R is H or alkyl (1-20C) and R' is alkyl (1-20C); in addition, this group may be attached to adjacent nucleotides through O or S. Not all linkages in an oligomer need to be identical.

Conjugation Protocols

The preferred conjugation protocol is based on a thiol-maleimide, a thiol-vinylsulfone, a thiol-bromoacetamide, or a thiol-iodoacetamide reaction that are facile at neutral or acidic pH. This obviates the need for higher pH conditions for conjugations as, for instance, would be necessitated when using active esters. Further details of exemplary conjugation protocols are described below in the Examples section.

Suitable routes of administration of the conjugates include, without limitation, oral, parenteral, rectal, transmucosal, intestinal administration, intramuscular, subcutaneous, intramedullary, intrathecal, direct intraventricular, intravenous, intravitreal, intraperitoneal, intranasal, or intraocular injections. The preferred routes of administration are parenteral. Alternatively, one may administer the compound in a local rather than systemic manner, for example, via injection of the compound directly into a solid tumor.

EXAMPLES

Various embodiments of the present invention are illustrated by the following examples, without limiting the scope thereof.

General

The intermediate Phe-Lys(MMT)-PABOH and the cross-linkers Phe-Lys(MMT)-PABOH, MC-Phe-Lys(MMT)-

PABOH and MC-Phe-Lys(MMT)-PABOCOO-PNP, where MC is maleimidocaproyl, Phe is phenylalanine, Lys is lysine, MMT is monomethoxytrityl, PABOH is p-aminobenzyl alcohol, and PNP is p-nitrophenyl moiety, were synthesized using a published method (Dubowchik et al., 2002). CPT-20-O-acyl derivatives of amino acids were prepared adapting a published method (Vishnuvajjala et al., U.S. Pat. No. 4,943,579). The azide precursors of CL1-SN-38, CL2-SN-38, and CL3-SN-38 shown in Schemes 1-3 have been described in the U.S. patent application corresponding to provisional U.S. Patent Application Ser. No. 60/885,325, filed on Jan. 17, 2007, the entire text of which is incorporated herein by reference. Abbreviations used below are: DCC, dicyclohexylcarbodiimide; NHS, N-hydroxysuccinimide, DMAP, 4-dimethylaminopyridine; PEG, polyethylene glycol. Flash chromatography was done using 230-400 mesh silica gel and methanol-dichloromethane gradient elution. Reverse phase HPLC was performed using a 7.8×300 mm C18 HPLC column, fitted with a precolumn filter, and using the solvent gradient of 100% solvent A to 100% solvent B in 10 minutes at a flow rate of 3 mL per minute and maintaining at 100% solvent B at a flow rate of 4.5 mL per minute for 5 or 10 minutes. Solvent A was 0.3% aqueous ammonium acetate, pH 4.46 while solvent B was 9:1 acetonitrile-aqueous ammonium acetate (0.3%), pH 4.46. HPLC was monitored by a dual in-line absorbance detector set at 360 nm and 254 nm.

Example 1

Preparation of CL1-SN-38

CL1-SN-38 is represented in Scheme-1. The azide precursor of CL1-SN-38 shown in the scheme has been described in the U.S. patent application corresponding to provisional U.S. Patent Application Ser. No. 60/885,325, filed on Jan. 17, 2007, the entire text of which is incorporated herein by reference. The reagent, namely 4-(N-maleimidomethyl)-N-(2-propynyl)cyclohexane-1-carboxamide, was prepared by reacting 0.107 g of SMCC and 0.021 mL of proparylamine (0.018 g; 1.01 equiv.) in dichloromethane using 1.1 equiv. of diisopropylethylamine. After 1 hr, the solvent was removed and the product was passed through a column of silica gel and eluted with 80:20 mixture of ethylacetate-hexane to obtain 83 mg of the product (colorless powder). Electrospray mass spectrum showed peaks at m/e 275 (M+H) and a base peak at m/e 192 in the positive ion mode, consistent with the structure calculated for $C_{15}H_{18}N_2O_3$: 275.1390 (M+H), found: 275.1394 (exact mass). A solution of the azide precursor (0.208 g) in DMSO (0.5 mL) was added to the acetylenic reagent (0.173 g; 3 equiv.), and more DMSO (1.5 mL) was added, followed by 1 mL of water, 0.05 M aqueous cupric sulfate (0.21 mL; 0.05 equiv. w.r.t azide) and 0.5 M aqueous sodium ascorbate (0.21 mL, 0.5 equiv. w.r.t. azide). The somewhat cloudy solution was stirred at ambient temperature for 1 hr. Solvents were removed under high vacuum, and the residual gummy material was purified by flash chromatography using methanol-dichloromethane (0-8%) gradient elution. The product, CL1-SN-38, was obtained in 65% yield. Reverse-phase HPLC (method 1): ret. time 9.55 min. Electrospray mass spectrum (positive ion mode) showed a peak at m/e 1283 (M+Na), consistent with the expected structure. Calculated for $C_{61}H_{81}N_9O_{20}$: 1260.5670 (M+H) and 1282.5490 (M+Na); found 1260.5688 (M+H) and 1282.5491 (M+Na).

Scheme-1

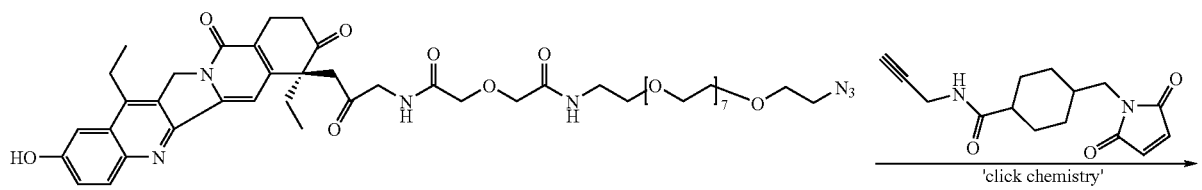

Azide precursor of CL1-SN-38

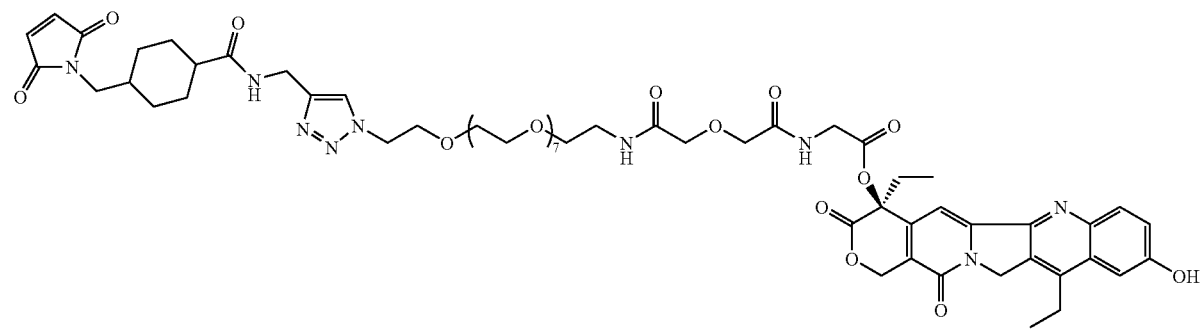

CL1-SN-38

Example 2

Preparation of CL2-SN-38

Synthesis is schematically shown in Scheme-2. The azide precursor of CL2-SN-38 shown in the scheme has been described in the U.S. patent application corresponding to provisional U.S. Patent Application Ser. No. 60/885,325, filed on Jan. 17, 2007, the entire text of which is incorporated herein by reference. The 'click chemistry' coupling of the azide precursor shown below with the acetylenic product described in Example 1 was carried out as follows. The azide (0.22 g, 0.127 mmol) and the acetylenic reagent (0.105 g, 0.38 mmol) were mixed in 3 mL of DMSO and 0.8 mL of water. Solid cuprous bromide (0.036 g, 2 equiv.) was added, and the heterogeneous mixture was stirred for 10 min. More water (0.7 mL) was added, and the reaction was continued for 40 min. Solvents were removed, and the crude product was purified by flash chromatography using methanol-dichloromethane gradient (2-8%) elution. The product was obtained in 47% yield. Reverse-phase HPLC (method 1): ret. time 13.35 min. Electrospray mass spectrum (positive ion mode) showed a peak at m/e 2022 (M+Na) consistent with the structure.

Calculated for $C_{107}H_{130}N_{12}O_{26}$: 1999.9292 (M+H) and 2021.9111 (M+Na); found 1999.9292 (M+H) and 2021.9114 (M+Na). The product was subjected to short-duration treatment with deprotection cocktail (trifluoroacetic acid (TFA) 2 mL, dichloromethane 0.5 mL, anisole 0.12 mL, and water 0.06 mL). Purification of crude product, after removal of TFA and solvents, was carried out by flash chromatography using methanol-dichloromethan (5% to 18%) gradient elution. The product, CL2-SN-38, had HPLC ret. time of 10.06 min. Yield: 56%. Electrospray mass spectrum (positive ion mode) showed peaks at m/e 1628 (M+H) and 1650 (M+Na), consistent with structure. Calculated for $C_{82}H_{106}N_{12}O_{23}$: 1627.7566 (M+H) and 1649.7386 (M+Na); found 1627.7585 (M+H) and 1649.7400 (M+Na).

Scheme-2
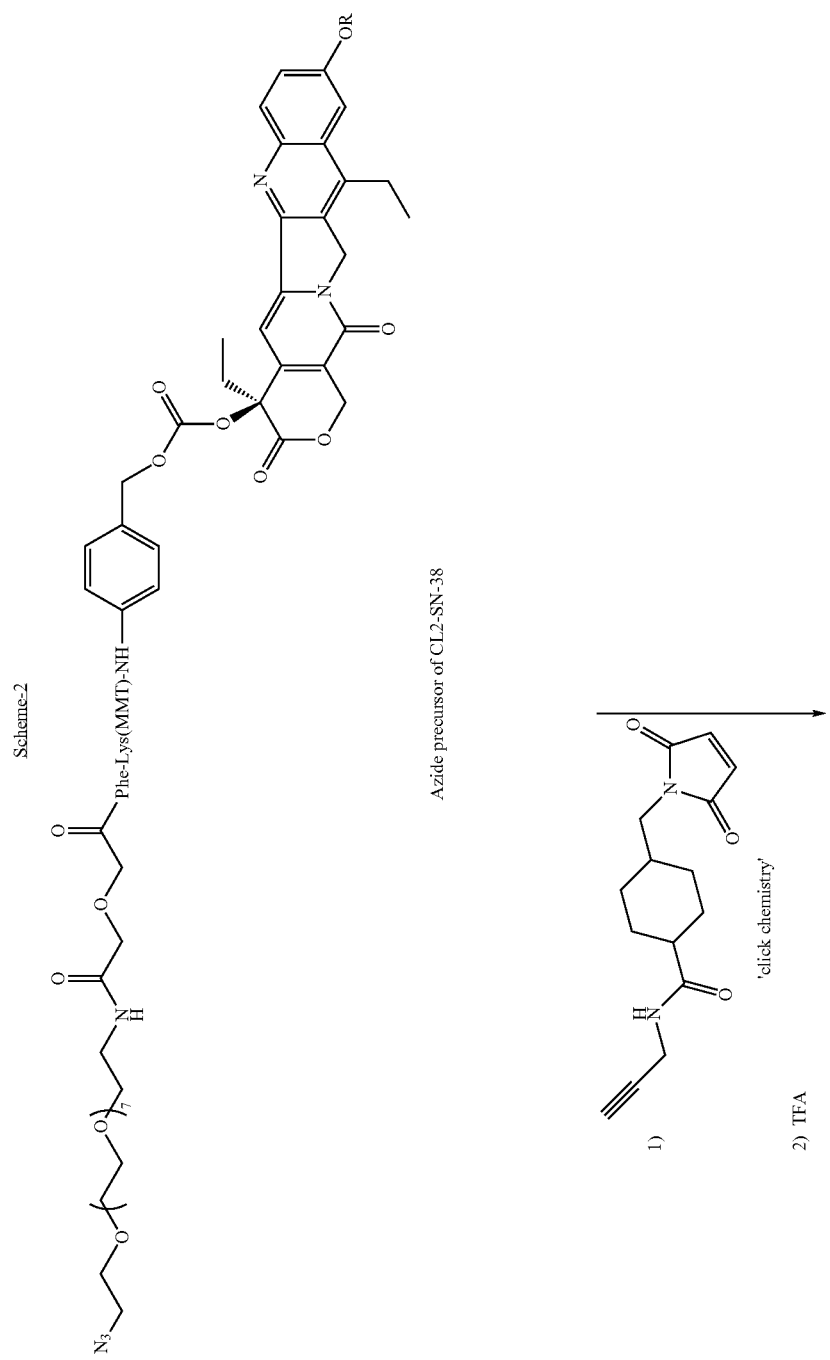
Azide precursor of CL2-SN-38
1) [maleimide-cyclohexyl-CONH-propargyl structure]
2) TFA
'click chemistry' →

-continued
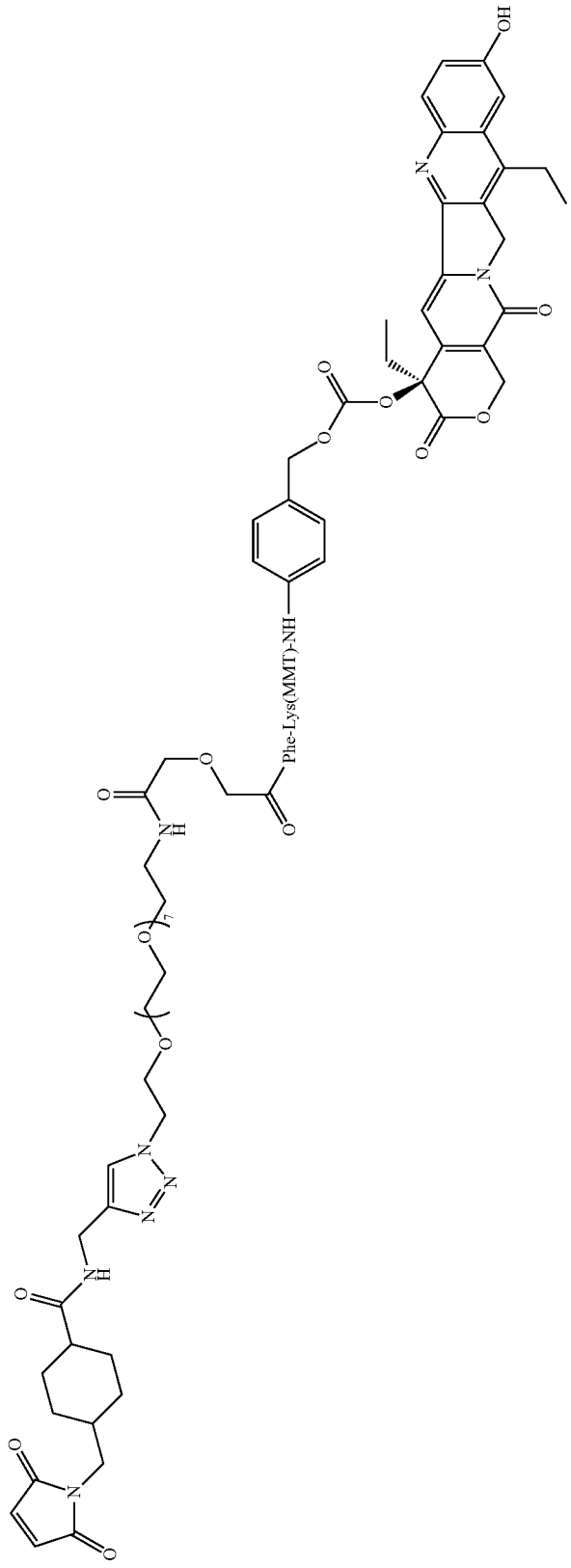
CL2-SN-38
(R=BOC)

Example 3

Preparation of CL3-SN-38

The azide precursor of CL3-SN-38 (shown in scheme-3 below) has been described in the U.S. patent application filed corresponding to provisional U.S. Patent Application Ser. No. 60/885,325, filed on Jan. 17, 2007, the entire text of which is incorporated herein by reference. The 'click chemistry' coupling of the azide precursor shown below with the acetylenic product described in Example 1 was carried out as follows. The azide (0.05 g, 0.03 mmol) and the acetylenic reagent (0.024 g, 0.087 mmol) were mixed in 1 mL of DMSO and 1 mL of water. Solid cuprous bromide (0.0045 g, 1 equiv.) was added, and the heterogeneous mixture was stirred for 1 hr. The crude product was precipitated by dilution with water, and purified by flash chromatography using methanol-dichloromethane gradient (2-10%) elution. The product was obtained in 76% yield. Reverse-phase HPLC (method 1): ret. time 11.65 min. Electrospray mass spectrum (positive ion mode) showed peak at m/e 1957 (M+H), consistent with structure.

Calculated for $C_{104}H_{125}N_{13}O_{25}$: 1956.8982 (M+H) and 1978.8801 (M+Na); found 1956.8926 (M+H) and 1978.8711 (M+Na). The product was subjected to short-duration treatment with deprotection cocktail (trifluoroacetic acid (TFA) 2 mL, dichloromethane 0.5 mL, anisole 0.12 mL, and water 0.06 mL). Purification of crude product, after removal of TFA and solvents, was carried out by precipitation in ethyl ether. The product, CL3-SN-38, had HPLC ret. time of 9.81 min. Yield: 90%. Electrospray mass spectrum (positive ion mode) showed peaks at m/e 1685 (M+H) and 1707 (M+Na), consistent with structure. Calculated for $C_{84}H_{109}N_{13}O_{24}$: 1684.7781 (M+H) and 1706.7600 (M+Na); found 1684.7778 (M+H) and 1706.7611 (M+Na).

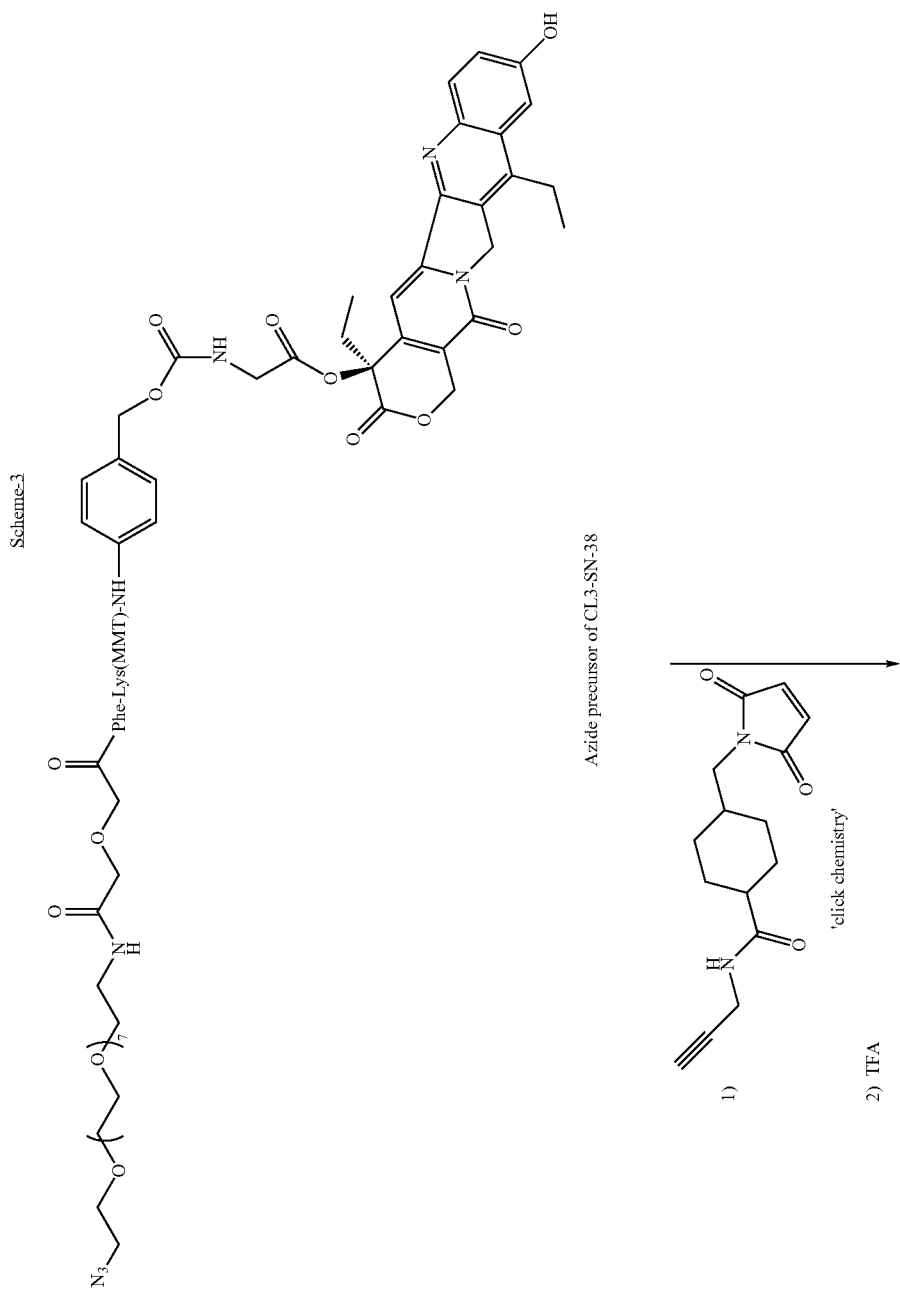

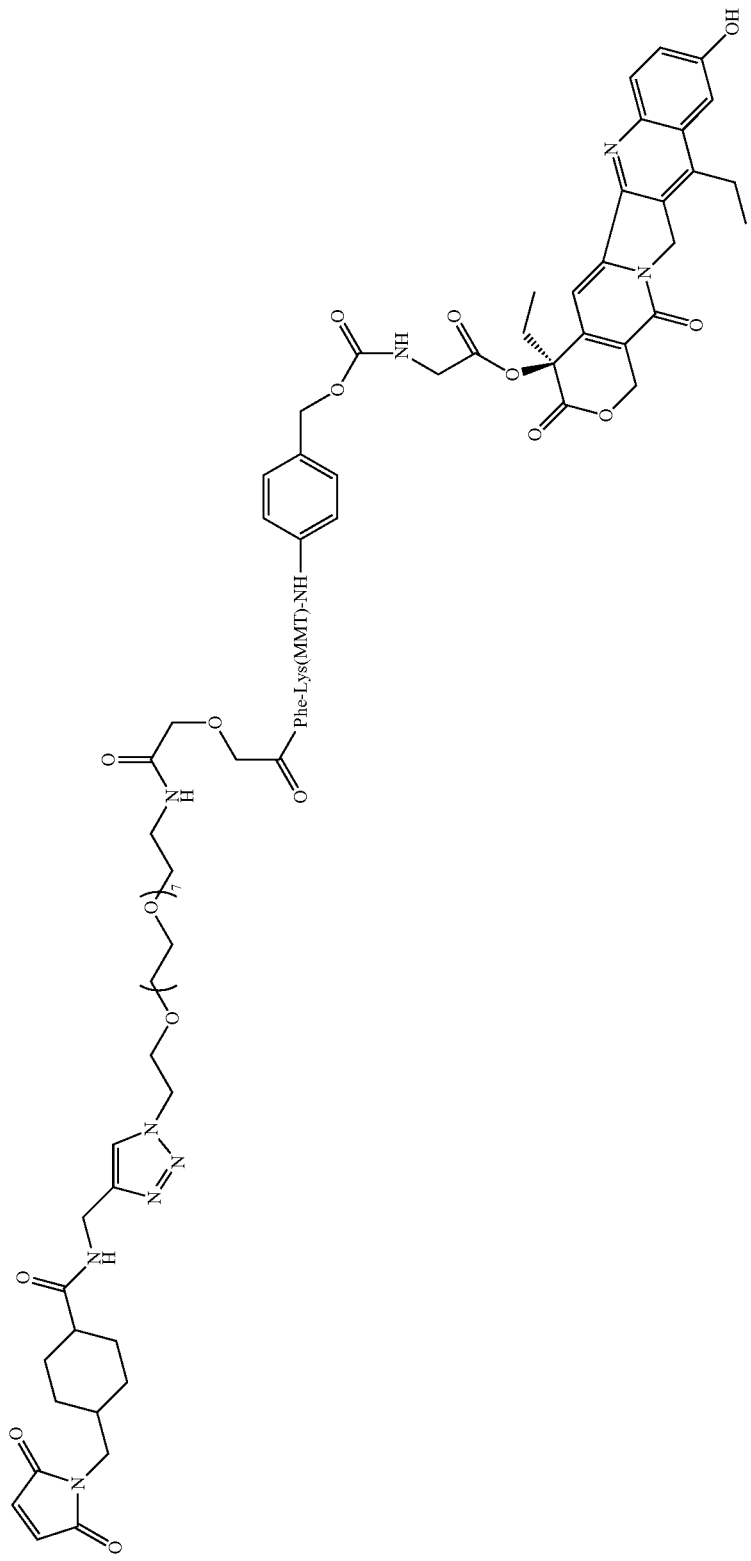

Example 4

Preparation of CL4-SN-38

Preparation is shown schematically in Scheme-4. The commercially available O-(2-azidoethyl)-O'-(N-diglycolyl-2-aminoethyl)heptaethyleneglycol was activated with NHS, DCC, and catalytic amount of DMAP, and reacted with p-aminobenzyl alcohol. The purified product was reacted with 10-O-BOC-SN38-20-O-chloroformate in the manner described for CL2-SN-38 preparation of Example 2. The purified product, obtained in 48% yield, had HPLC ret. time of 12.11 min. Electrospray mass spectrum showed m/e at 1179 (M+H). Calculated for $C_{57}H_{75}N_7O_{20}$: 1178.5139 (M+H) and 1200.4959 (M+Na); found 1178.5138 (M+H) and 1200.4944 (M+Na). The azide precursor (0.14 g) and the acetylenic reagent (0.1 g, 3 equiv) were mixed in 3 mL of DMSO and 1 mL of water. Solid cuprous bromide (0.05 g, 3 equiv.) was added, and the heterogeneous mixture was stirred for 10 min. More water (0.5 mL) was added, and the reaction was continued for 30 min. Solvents were removed, and the crude product was purified by flash chromatography using methanol-dichloromethane gradient (0-8%) elution. The product obtained (0.135 g; 84% yield) had HPLC ret time of ret. time 11.5 min. Calculated for $C_{72}H_{93}N_9O_{23}$: 1452.6457 (M+H) and 1474.6276 (M+Na); found 1452.6429 (M+H) and 1474.6262 (M+Na). The product was subjected to short-duration treatment with deprotection cocktail as described in Example 2. Purification of crude product, after removal of TFA and solvents, was carried out by flash chromatography using methanol-dichloromethan (1% to 8%) gradient elution. The product, CL4-SN-38, had HPLC ret. time of 10.31 min. Yield: 56%. Electrospray mass spectrum (positive ion mode) showed peaks at m/e 1353 (M+H), consistent with structure. Calculated for $C_{67}H_{85}N_9O_{21}$: 1352.5932 (M+H) and 1374.5752 (M+Na); found 1352.5907 (M+H) and 1374.5729 (M+Na).

Scheme-4

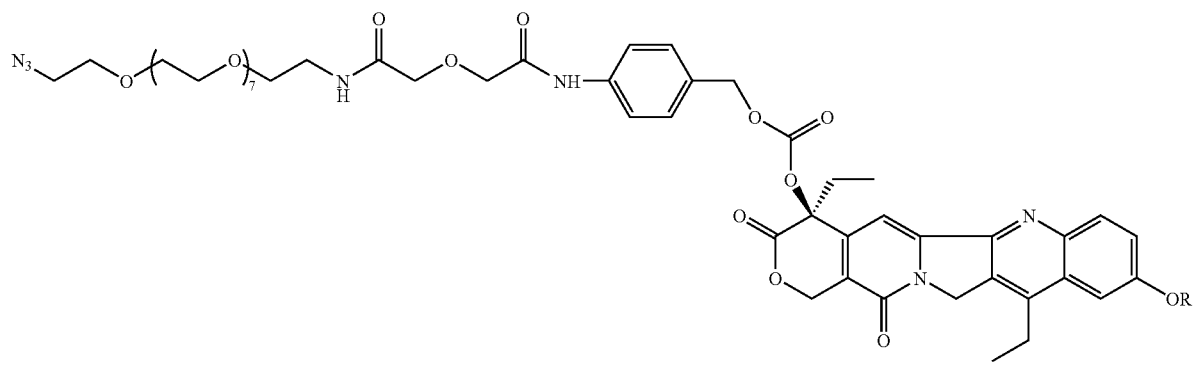

Azide precursor of CL4-SN-38

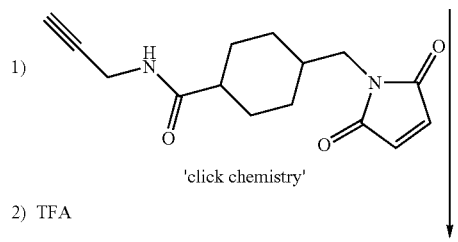

1)

'click chemistry'

2) TFA

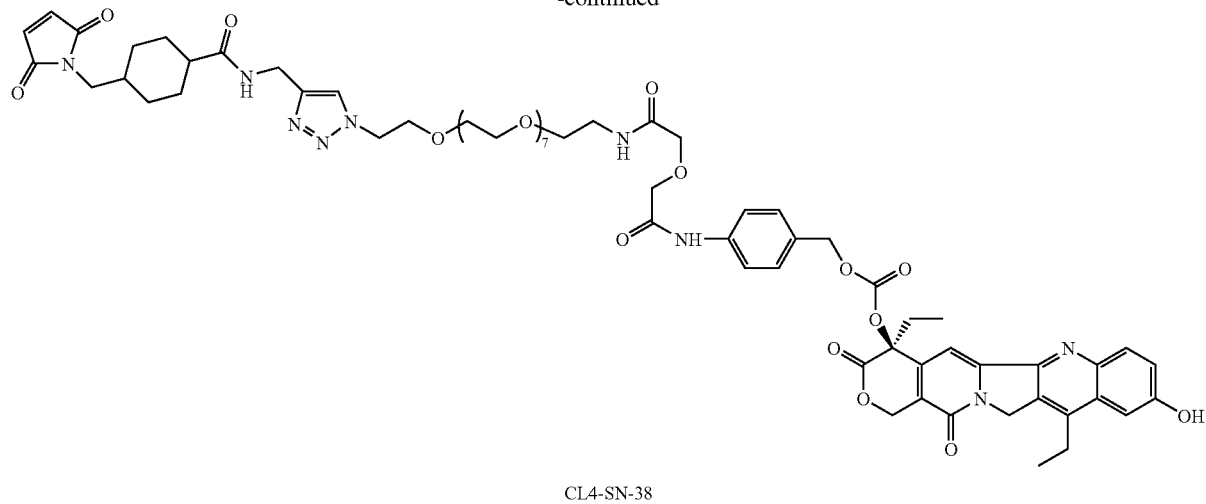

CL4-SN-38
(R = BOC)

Example 5

Preparation of CL5-SN-38

The azide precursor for this substrate was prepared in 3 steps from SN-38, involving protection of 10-OH group as 10-O-BOC derivative, followed by 20-O-chloroformate formation and reaction with O-(2-azidoethyl) heptaethyleneglycol. The azido-SN-38 product was purified by flash chromatography in the manner described in Example 2. The product, with HPLC ret. time: 12.4 min, also contained ~8.5% of unremoved starting material. The electrospray mass spectrum of this material showed m/e at 915 (M+H). Calculated for $C_{44}H_{59}N_5O_{16}$: 914.4036 (M+H); found 914.4034 (M+H). The click chemistry coupling of this azido derivative with the acetylenic reagent of Example 1 was carried out with 3 equivalents of the latter and 3 equivalents of cuprous bromide in a mixture of DMSO and water (1:1 v/v), and purified by flash chromatography. Yield: 81%. HPLC ret time: 11.62 min. Electrospray mass spectrum (positive ion mode) showed peaks at m/e 1189 (M+H), consistent with structure. Calculated for $C_{59}H_{77}N_7O_{19}$: 1188.5354 (M+H); found 1188.5323 (M+H). Deprotection using trifluoroacetic acid using conditions described in Example 2, followed by flash chromatographic purification yielded the title product (CL5-SN-38). HPLC: ret. time 10.28 min. Electrospray mass spectrum (positive ion mode) showed peaks at m/e 1089 (M+H), consistent with structure. Calculated for $C_{54}H_{69}N_7O_{17}$: 1088.4822 (M+H) and 1110.4642 (M+Na); found 1088.4799 (M+H) and 1110.4632 (M+Na).

Scheme-5

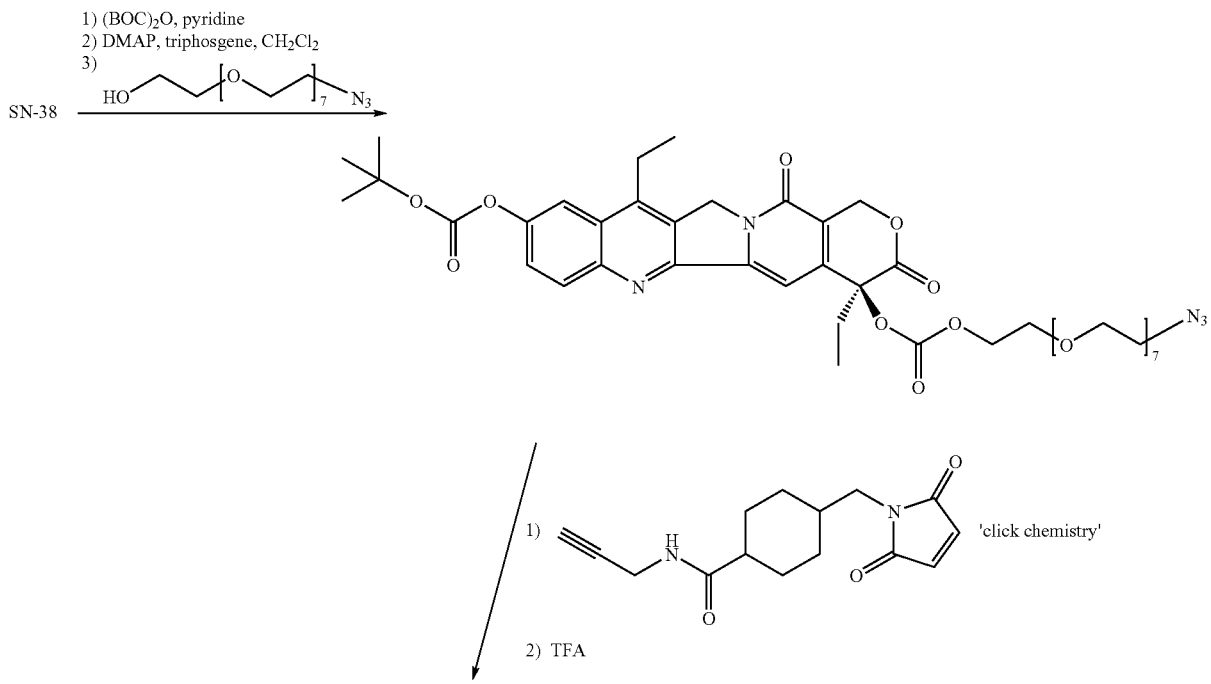

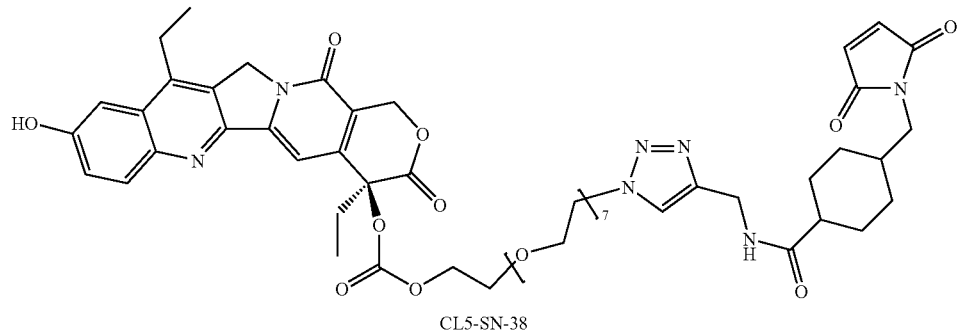

CL5-SN-38

Example 6

Preparations of CL1-SN-38-10-O-COR, CL2-SN-38-10-O-COR, CL3-SN-38-10-O-COR, CL4-SN-38-10-O-COR, and CL5-SN-38-10-O-COR This Example shows that the 10-OH group of SN-38 is protected as a carbonate or an ester, instead of as 'BOC', such that the final product is ready for conjugation to antibodies without a need for deprotecting the 10-OH protecting group. This aspect has been described in paragraph 0065. This group is readily deprotected under physiological pH conditions after in vivo administration of the protein conjugate. In Scheme-6, 'R' can be a substituted alkyl such as $(CH_2)_n$—N$(CH_3)_2$ where n is 2-10, or simple alkyl such as $(CH_2)_n$—$CH_3$ where n is 0-10, or it can be alkoxy moiety such as "$CH_3$$(CH_2)_n$—O—" where n is 0-10 or substituted alkoxy moiety such as such as O—$(CH_2)_n$—N$(CH_3)_2$ where n is 2-10 and wherein the terminal amino group is optionally in the form of a quaternary salt for enhanced aqueous solubility, or it is a methoxy PEG residue. In the simplest version of the latter category, R "—O—$(CH_2)_2$—$OCH_3$". These 10-hydroxy derivatives are readily prepared by treatment with the chloroformate of the chosen reagent, if the final derivative is to be a carbonate. Typically, the 10-hydroxy-containing camptothecin such as SN-38 is treated with a molar equivalent of the chloroformate in dimethylformamide using triethylamine as the base. Under these conditions, the 20-OH position is unaffected. For forming 10-O-esters, the acid chloride of the chosen reagent is used. In each case, the sequence of steps, after 10-hydroxy derivatization, described in Examples 1-5 is followed to generate 10-protected versions of CL1-SN-38, CL2-SN-38, CL-3-SN-38, CL4-SN-38, and CL5-SN-38, respectively. For the simplest case of R being ethoxy, the first step is the conversion of SN-38 to its 10-O-ethyl carbonate by treatment with ethyl chloroformate in dimethylformamide using triethylamine as the base.

Scheme-6
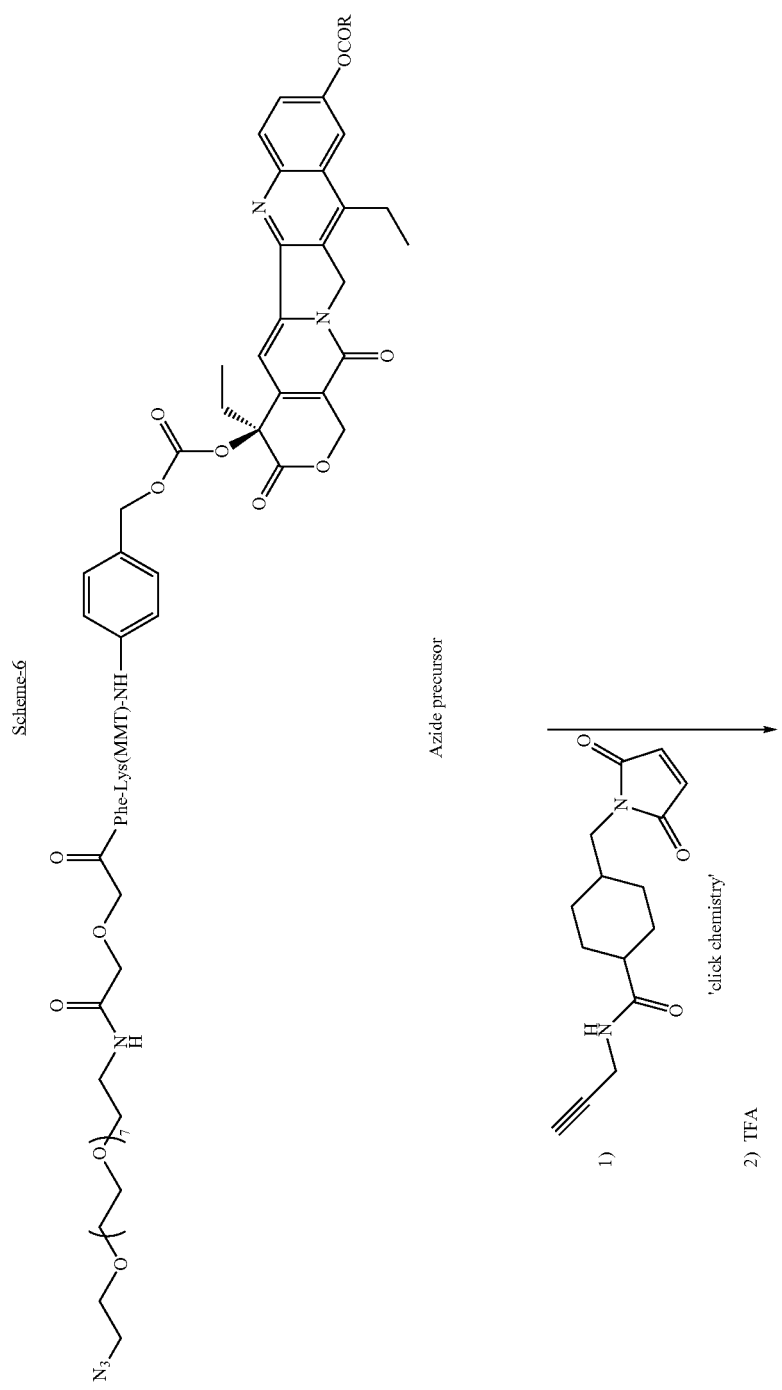

-continued
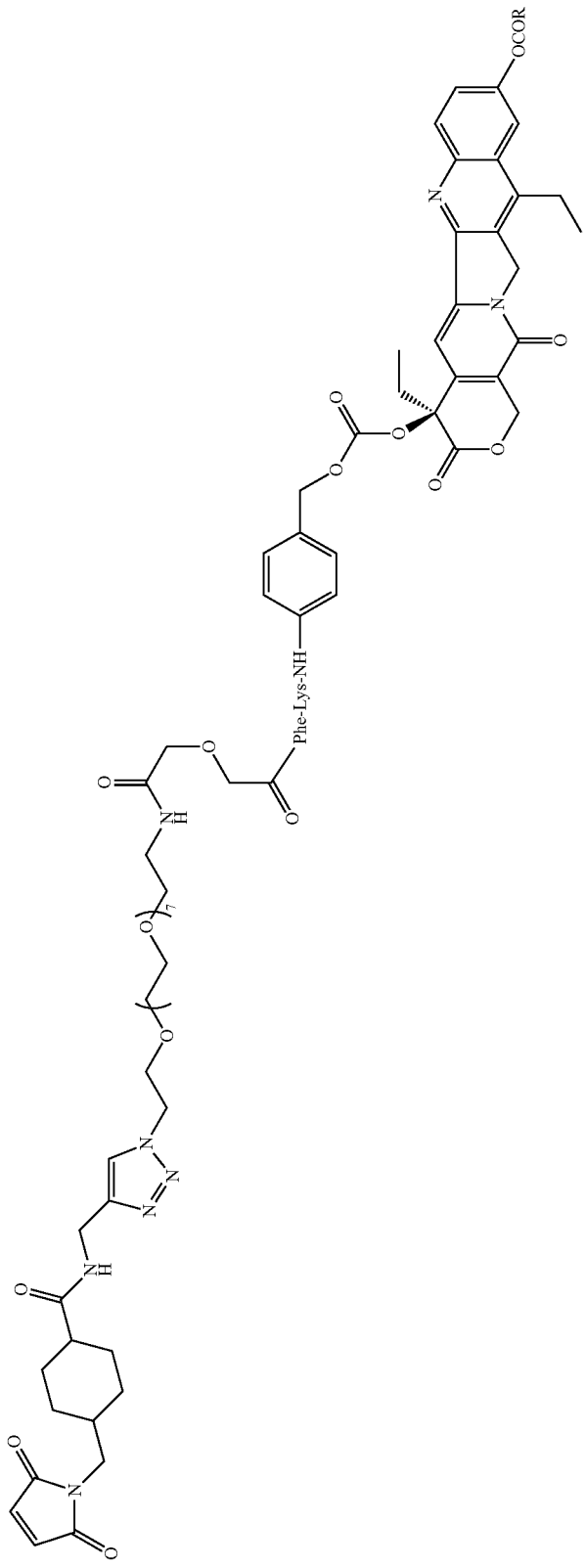
CL2-SN38-10-O-COR

Example 7

Conjugation of Maleimide-Containing SN-38 Intermediates to Mildly Reduced Antibodies: Attachment to Interchain Region of MAbs The anti-CEACAM5 humanized MAb, hMN14, the anti-CD22 humanized MAb, hLL2, the anti-CD20 humanized MAb, hA20, the anti-EGP-1 humanized MAb, hRS7, and anti-MUC1 humanized MAb, hPAM4, were used in these studies. Each antibody was reduced with dithiothreitol (DTT), used in a 50-to-70-fold molar excess, in 40 mM PBS, pH 7.4, containing 5.4 mM EDTA, at 37° C. (bath) for 45 min. The reduced product was purified on centrifuged size-exclusion column and buffer-exchanged with 75 mM sodium acetate-1 mM EDTA. The thiol content was determined by Ellman's assay, and was in the 6.5-to-8.5 SH/IgG range. Alternatively, the antibodies are reduced with tris (2-carboxyethyl) phosphine (TCEP) in phosphate buffer at pH in the range of 5-7, followed by in situ conjugation. The reduced MAb was reacted with ~10-to-15-fold molar excess of 'CL1-SN-38' of Example 1, or 'CL2-SN-38' of Example 2, or 'CL3-SN-38' of Example 3, or 'CL4-SN-38' of Example 4, or 'CL5-SN-38' of Example 5, or 'CL2-SN-38-10-O-CO$_2$Et' of Example 6, using DMSO at 10% v/v as co-solvent, and incubating for 20 min at ambient temperature. The conjugate was purified by centrifuged SEC, passage through a hydrophobic column, and finally by ultrafiltration-diafiltration. The product was assayed for SN-38 by absorbance at 366 nm and correlating with standard values, while the protein concentration was deduced from absorbance at 280 nm, corrected for spillover of SN-38 absorbance at this wavelength. This way, the SN-38/MAb substitution ratios were determined. The purified conjugates were stored as lyophilized formulations in glass vials, capped under vacuum and stored in a −20° C. freezer. SN-38 molar substitution ratios (MSR) obtained for some of these conjugates, which are typically in the 5-to-7 range in view of the mode of conjugation, are shown in Table 2.

TABLE 2

SN-38/MAb Molar substitution ratios (MSR) in some conjugates

| MAb | Conjugate | MSR |
| --- | --- | --- |
| hMN-14 | hMN-14-[CL1-SN-38], using drug-linker of Example 1 | 7.7 |
|  | hMN-14-[CL2-SN-38], using drug-linker of Example 2 | 6.8 |
|  | hMN-14-[CL3-SN-38], using drug-linker of Example 3 | 5.5 |
|  | hMN-14-[CL5-SN-38], using drug-linker of Example 5 | 6.9 |
| hRS7 | hRS7-CL1-SN-38 using drug-linker of Example 1 | 5.3 |
|  | hRS7-CL2-SN-38, using drug-linker of Example 2 | 6.3 |
|  | hRS7-CL3-SN-38, using drug-linker of Example 3 | 5.1 |
| hPAM-4 | hPAM-4-[CL2-SN-38], using drug-linker of Example 2 | 5.7 |
| hLL2 | hLL2-CL1-SN-38, using drug-linker of Example 1 | 7.4 |
|  | hLL2-CL2-SN-38, using drug-linker of Example 2 | 6.4 |
| hA20 | hA20-CL2-SN-38, using drug-linker of Example 2 | 6.1 |

Example 8

In Vitro Hydrolytic Stabilities of Different hMAb-SN-38 Conjugates: Fine-Tuning of Stability Profiles by Varying the Linker and Modifying 10-Hydroxy Position In vitro stabilities of SN-38 conjugates of anti-CEACAM5 antibody, hMN-14, derived from CL1-SN-38 of Example 1, CL2-SN-38 of Example 2, CL3-SN-38 of Example 3, CL4-SN-38 of Example 4, CL5-SN-38 of Example 5, and the 10-O-ethoxycarbonyl analog of CL2-SN-38, as described in Example 6 were examined in 40 mM PBS at 37° C. At periodic intervals, aliquots were withdrawn, a known amount of 10-hydroxycamptothecin used as an internal standard was added, and the material was extracted by protein precipitation with acetonitrile, and extraction of SN-38 (dissociated from antibody) by extraction with chloroform. Fixed volumes of the extracts were analyzed by reverse phase HPLC, quantifying for SN-38 by fluorescence detection of HPLC peaks. SN-38/internal standard peak ratios were correlated with SN-38 standard curve, the latter generated by plotting SN-38/internal standard peak ratios as a function of SN-38 concentration. Plots of SN-38 dissociation kinetics were generated using standard Prism® software. FIG. 1 shows that steric hindrance around 20-carbonate or 20-ester position in SN-38 enhances hydrolytic stability of the corresponding antibody conjugates. In addition, protection of 10-hydroxy position of SN-38, as ethoxycarbonyl derivative, for instance (as shown in this Example), significantly enhances hydrolytic stability. Examples of 10-hydroxy protecting groups are enumerated in paragraph 053. Thus, modulating the stability profiles of camptothecin conjugates in general, and of SN-38 conjugates in particular, by variations in linker design as described in these Examples, is also an embodiment of the present invention.

Example 9

In Vitro Cell-Binding and Cytotoxicity of Antibody-SN-38 Conjugates in Different Cell Lines In vitro studies were conducted using LoVo human colon carcinoma cells and anti-CEACAM5 antibody conjugates of SN-38 [hMN-14-(CL1-SN-38), hMN-14-(CL2-SN-38), and hMN-14-(CL3-SN38)], CaPan-1 human pancreatic cell line (for which anti-EGP-1 antibody hRS7 is positive) and Calu-3 lung adenocarcinoma cell line and hRS7 conjugates. In the latter two cell lines, the conjugates used were hRS7-CL1-SN-38, hRS7-CL2-SN-38, and hRS7-CL3-SN-38. Cell lines were obtained from American Type Culture Collection (ATCC, Rockville, Md.). For cell-binding assays, unmodified antibodies were used as positive controls. In growth inhibition (cytotoxicity) assays, free SN-38 drug was used as positive control. Cell-binding to antigen-positive tissue culture cell lines was done by indirect cell surface binding ELISA assays. For growth inhibition studies, cells were harvested and plated into 96 well plates (25,000 cells/well). 20 μL of serially diluted solutions of conjugates or controls were added to each well to final concentration of 0-7 μM final concentration of SN-38 equivalent, and incubated at 37° C. Total incubation time was 96 h. MTS dye reduction assay was used to determine dose response curves, and effective $EC_{50}$ concentrations were determined using PrismPad® Software (Advanced Graphics Software, Encinitas, Calif.). Similarly, Capan-1 human pancreatic cell line was used for evaluation of SN-38 conjugates of anti MUC-1 antibody, hPAM4, which is specific for this cell line. This shows preservation of cell-binding and cytotoxicity of SN-38 conjugates of hPAM-4. In a similar fashion, cell-binding and cytotoxicities of CL4-SN-38, CL5-SN-38, and 10-ethoxycarbonyl analogs of CL1-SN-38, CL2-SN-38, CL3-SN-38, CL4-SN-38, and CL5-SN-38 conjugates of these antibodies show cell-bindings and growth inhibitions when these are examined in the cell lines for which the antibodies are specific.

Figure 2:
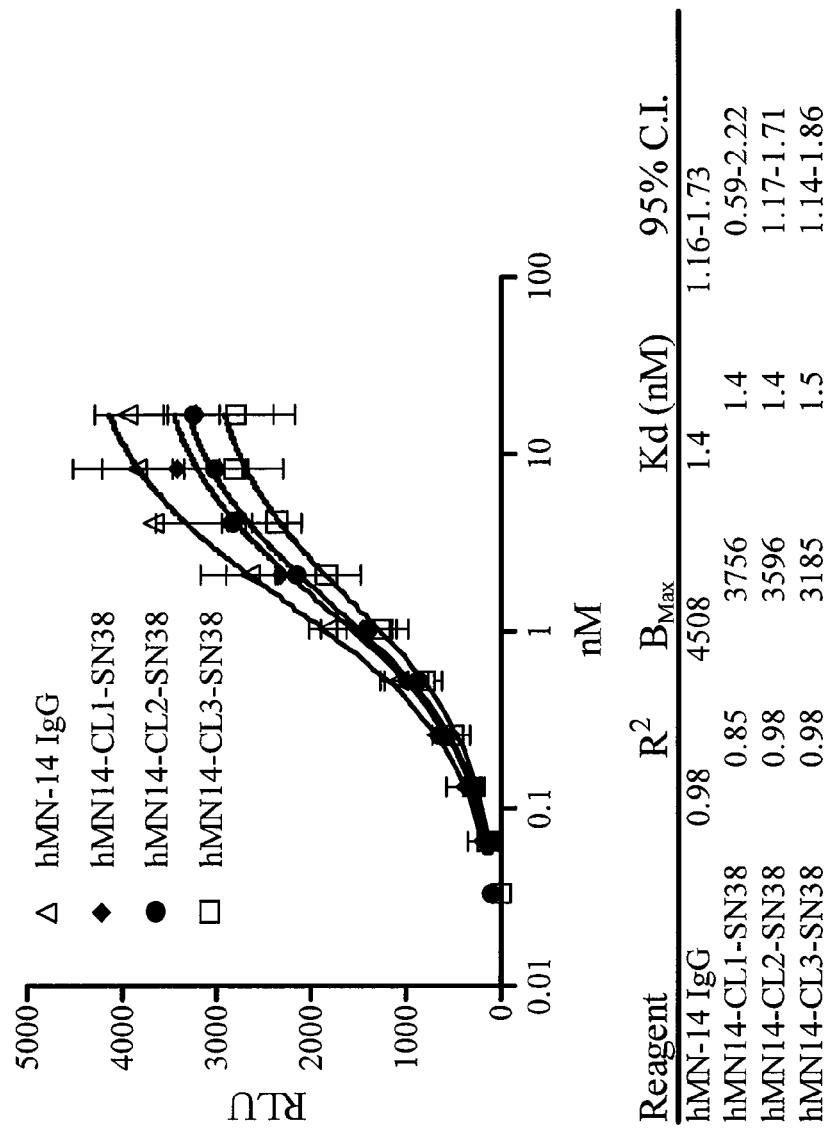
FIG. 2. Cell binding of various hMN14-SN38 immunoconjugates on a human colorectal adenocarcinoma cell line LoVo.
Figure 3:
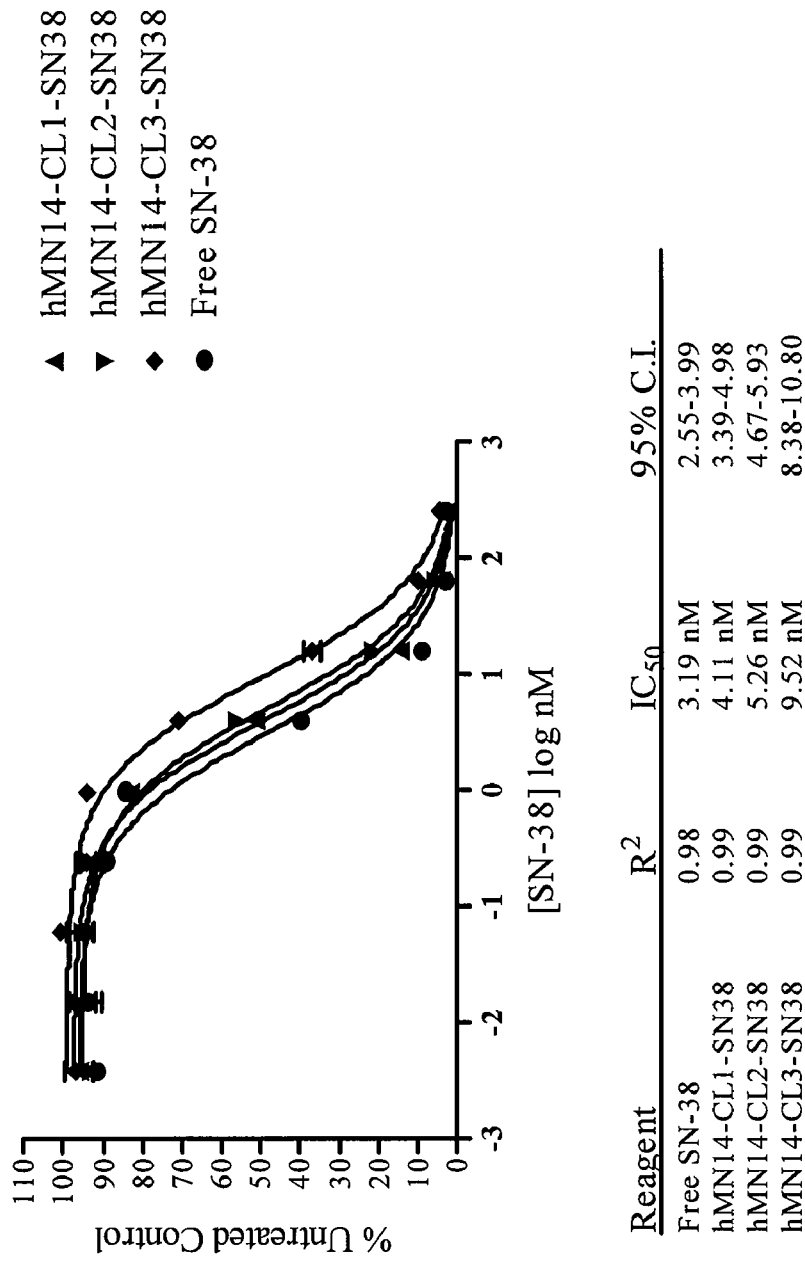
FIG. 3. In vitro cytotoxicity of various hMN14-SN38 immunoconjugates on a human colorectal adenocarcinoma cell line LoVo.
Figure 4:
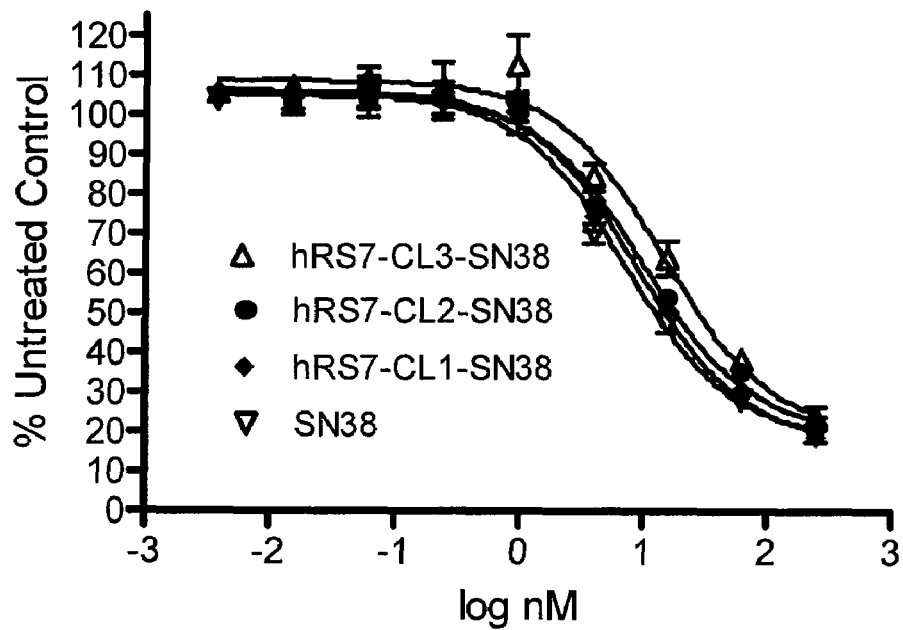
FIG. 4. Cytotoxicity against lung adenocarcinoma (Calu-3).

The following figures demonstrate antigen-binding and growth inhibiting capacity of exemplary conjugates. FIG. 2 shows binding of various hMN14-SN38 immunoconjugates to the LoVo human colorectal adenocarcinoma cell line. The CL-1, CL-2 and CL3 conjugates of SN38 to hMN14 showed binding affinities ($K_d$ values) that were comparable to the unconjugated hMN-14 IgG. FIG. 3 shows the in vitro cytotoxicity of hMN14-SN38 immunoconjugates on the LoVo cell line. The CL1, CL2 and CL3 SN38 conjugates of hMN14 exhibited comparable cytotoxicities (exemplified by $IC_{50}$ values) with free SN-38. The skilled artisan will realize that in vivo the cytotoxicity of free SN-38 will be limited by its systemic toxicity, while the antibody-targeted delivery of conjugated SN-38 will reduce systemic toxicity and allow higher effective doses of SN-38 to be delivered to the target cells or tissues. FIG. 4 illustrates cytotoxicity against the Calu-3 lung adenocarcinoma cell line. The CL1, CL2 and CL3 conjugates of hRS7 showed $EC_{50}$ values that were comparable with free SN38.

Example 10

Figure 5:
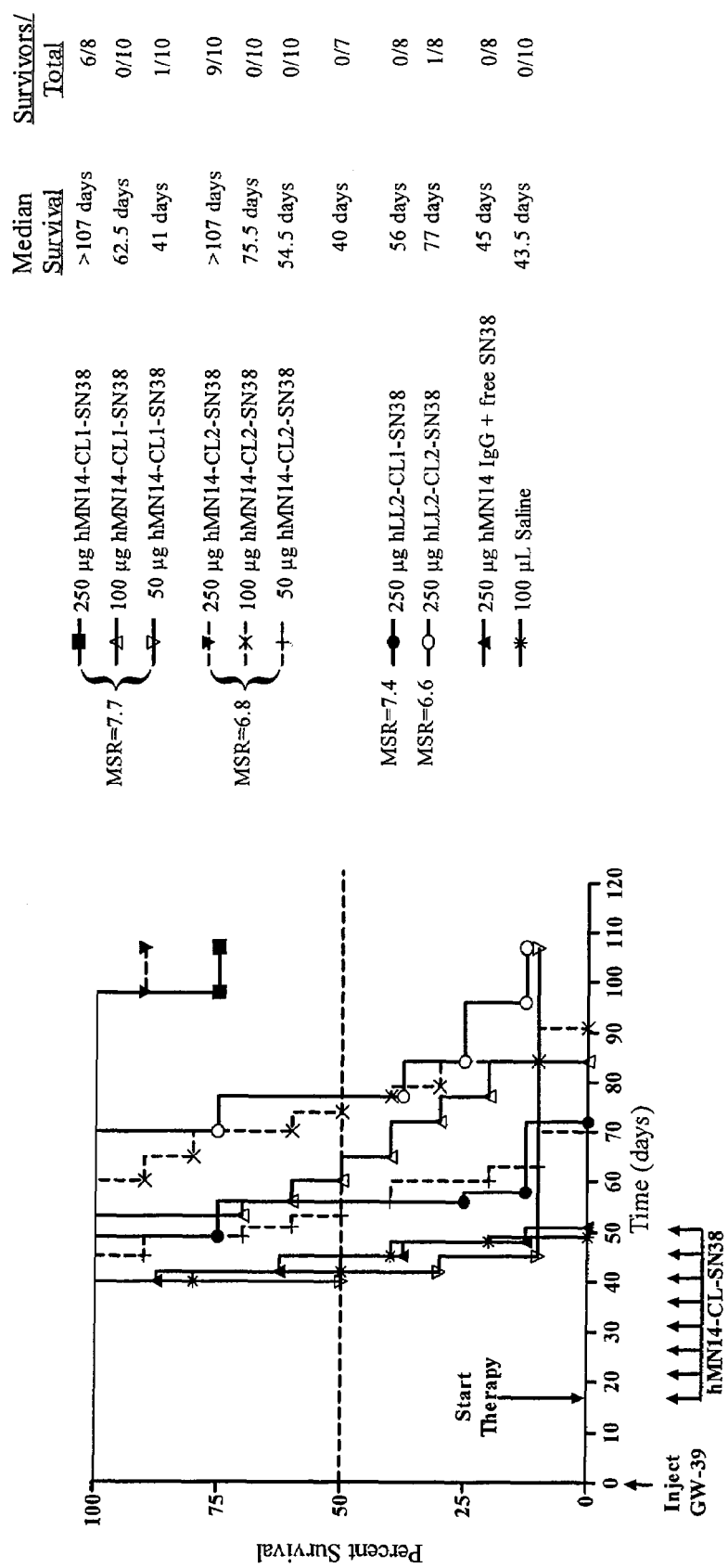
FIG. 5. Survival curves of hMN14-CL-SN38 treated mice bearing GW-39 lung metastatic disease.

In Vivo Therapy of Lung Metastases of GW-39 Human Colonic Tumors in Nude Mice Using hMN-14-[CL1-SN-38] and hMN-14-[CL2-SN-38] with Appropriate Controls A lung metastatic model of colonic carcinoma was established in nude mice by i.v. injection of GW-39 human colonic tumor suspension, and therapy was initiated 14 days later. Specific anti-CEACAM5 antibody conjugates, hMN14-CL1-SN-38 and hMN-14-CL2-SN-38, as well as nontargeting anti-CD22 MAb control conjugates, hLL2-CL1-SN-38 and hLL2-CL2-SN-38 and equidose mixtures of hMN14 and SN-38 were injected at a dose schedule of q4dx8, using different doses. FIG. 5 (MSR=SN-38/antibody molar substitution ratio) shows selective therapeutic effects due to hMN-14 conjugates. At equivalent dosages of 250 µg, the mice treated with hMN14-CL1-SN38 or hMN14-CL2-SN38 showed a median survival of greater than 107 days. Mice treated with the control conjugated antibodies hLL2-CL1-SN38 and hLL2-CL2-SN38, which do not specifically target lung cancer cells, showed median survival of 56 and 77 days, while mice treated with unconjugated hMN14 IgG and free SN38 showed a median survival of 45 days, comparable to the untreated saline control of 43.5 days. A significant and surprising increase in effectiveness of the conjugated, cancer cell targeted antibody-SN38 conjugate, which was substantially more effective than unconjugated antibody and free chemotherapeutic agent alone, was clearly seen. The dose-responsiveness of therapeutic effect of conjugated antibody was also observed. These results demonstrate the clear superiority of the SN38-antibody conjugates compared to the combined effect of both unconjugated antibody and free SN38 in the same in vivo human lung cancer system.

Example 11

In Vivo Therapy of Nude Mice Carrying CaPan1 Human Pancreatic Tumors Using hPAM-4-[CL2-SN-38]

Figure 6:
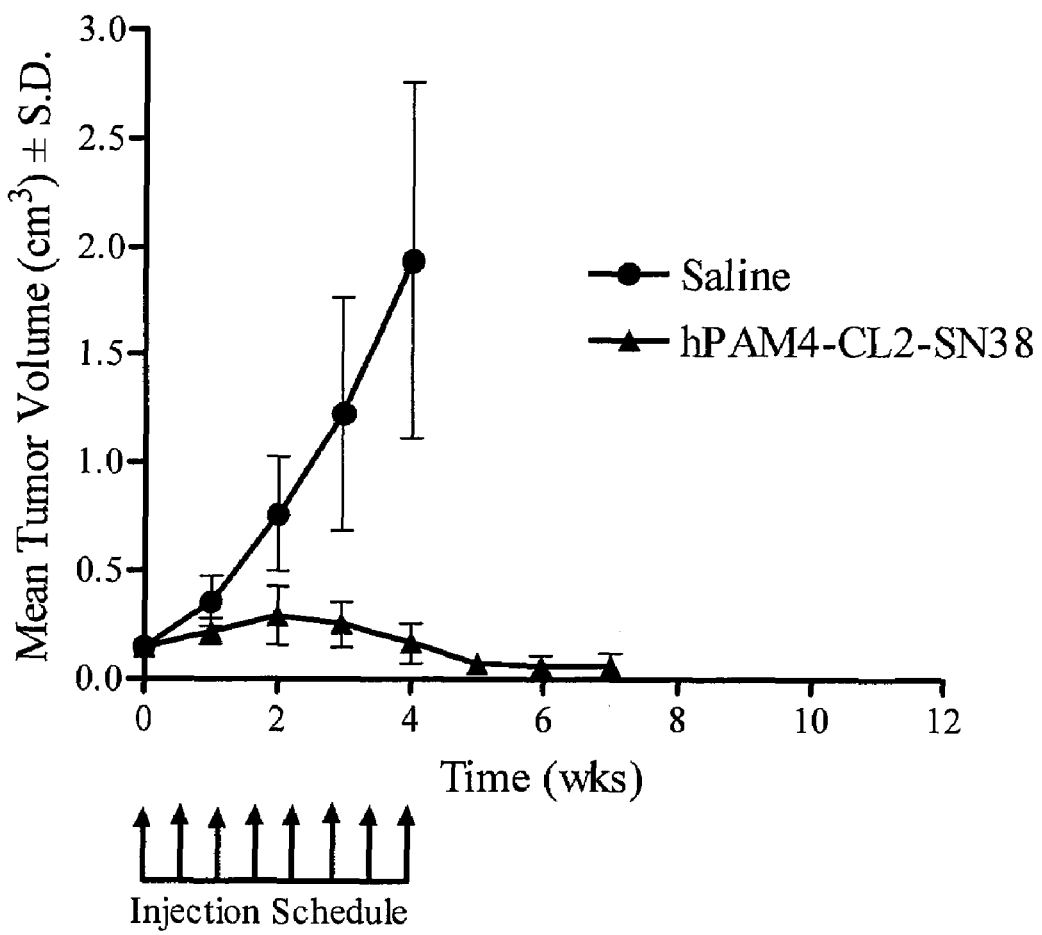
FIG. 6. Therapeutic efficacy of hPAM4-CL2-SN38 in CaPan1 tumor-bearing mice (n=4) (500 µg, q4dx8).

A s.c. pancreatic tumor model was established using human CaPan1 human tumor cells, and after the tumor volumes reached ~0.2 cm$^3$, therapy was initiated using the SN-38 conjugate of specific antibody, hPAM4, namely, hPAM4-CL2-SN-38. A dose schedule of q4dx8 using the protein dose of 0.5 mg (drug dose of ~0.39 mg of conjugated SN-38/kg of body weight) showed significant (treated vs. untreated week-3: $P_{AUC}$<0.01) tumor growth control versus untreated (FIG. 6). All treated mice were alive >7 weeks, while all untreated mice were sacrificed by 4½ weeks due to tumor burden. The mice treated with hPAM4-CL2-SN38 conjugated antibody showed a mean tumor volume of close to zero after 7 weeks (FIG. 6), while point control mice had a mean tumor volume of almost 2.0 cm$^3$ after 4 weeks. The hPAM4-CL2-SN38 antibody conjugate was highly effective at reducing tumor burden and prolonging survival in this in vivo human pancreatic cancer model system.

Example 12

Elimination of HIV Infection by Treatment with a SN-38 Conjugate of an Anti-gp120 MAb A MAb targeted to the HIV envelope protein gp120, anti-gp120 antibody such as P4/D10, is reduced using conditions described in Example 7, and the reduced MAb is reacted with a 20-fold molar excess of the drug linker CL2-SN-38, which is as described for Example 2. An anti-gp120-SN-38 conjugate with a substitution of ~8 drug molecules per antibody is obtained. An in vitro HIV-inhibition assay with said conjugate is performed by using various mixtures of uninfected Jurkat-T cells and fully HIV-infected Jurkat T-cells (in the ratios of 99.8:2 to 95:5), and treating with serial dilutions of the conjugate, non-specific hRS7-CL-SN38 conjugate control, naked antibody, and HIV-negative serum from 100 to 0.00001 µg/mL. The cells so treated are incubated in RPMI 1640 culture medium at 37° C. for seven days, and then assayed for HIV inhibition by the relevant ELISA test. This experiment shows a strong and specific inhibition of intercellular spread of HIV by the specific drug conjugate. The in vivo efficacy is tested by administering mice with isologous HIV-infected cells together with specific and non-specific SN-38 conjugates. For this, primary murine splenocytes infected by HIV-1/MuLV pseudotype virus are intraperitoneally transferred to groups of mice simultaneously with immunoconjugate administration. Peritoneal cells are harvested 10 days later. While infectious HIV presence is demonstrated in control mice, no infectious HIV is detected in mice treated with 100 µg or less of anti-gp120-SN-38 conjugate. No protection is seen with mice treated with control conjugates.

From the foregoing description, one skilled in the art can easily ascertain the essential characteristics of this invention, and without departing from the spirit and scope thereof, can make various changes and modifications of the invention to adapt it to various usage and conditions without undue experimentation. All patents, patent applications and publications cited herein are incorporated by reference in their entirety.

What is claimed is:
1. A conjugate of a camptothecin drug and a targeting moiety, wherein the conjugate has a structural formulae selected from the group consisting of MAb-CL1-SN-38, MAb-CL2-SN-38, MAb-CL3-SN-38, MAb-CL4-SN-38, MAb-CL5-SN-38 and having a structure selected from:
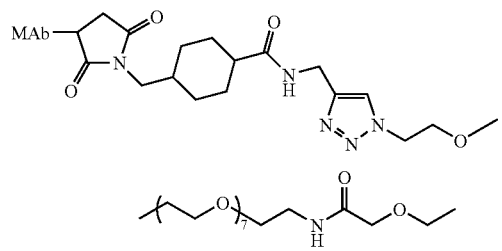
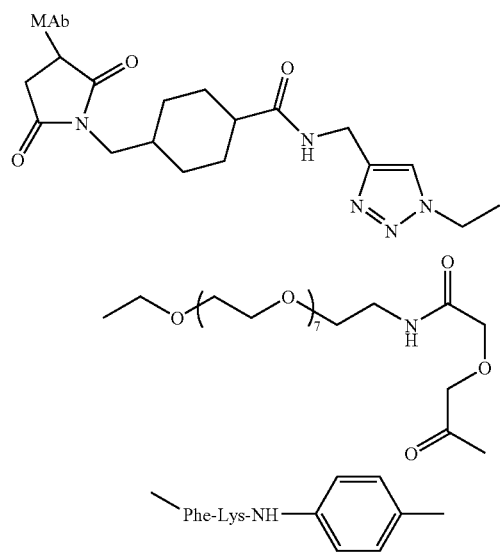
MAb-CL1-SN-38
MAb-CL2-SN-38
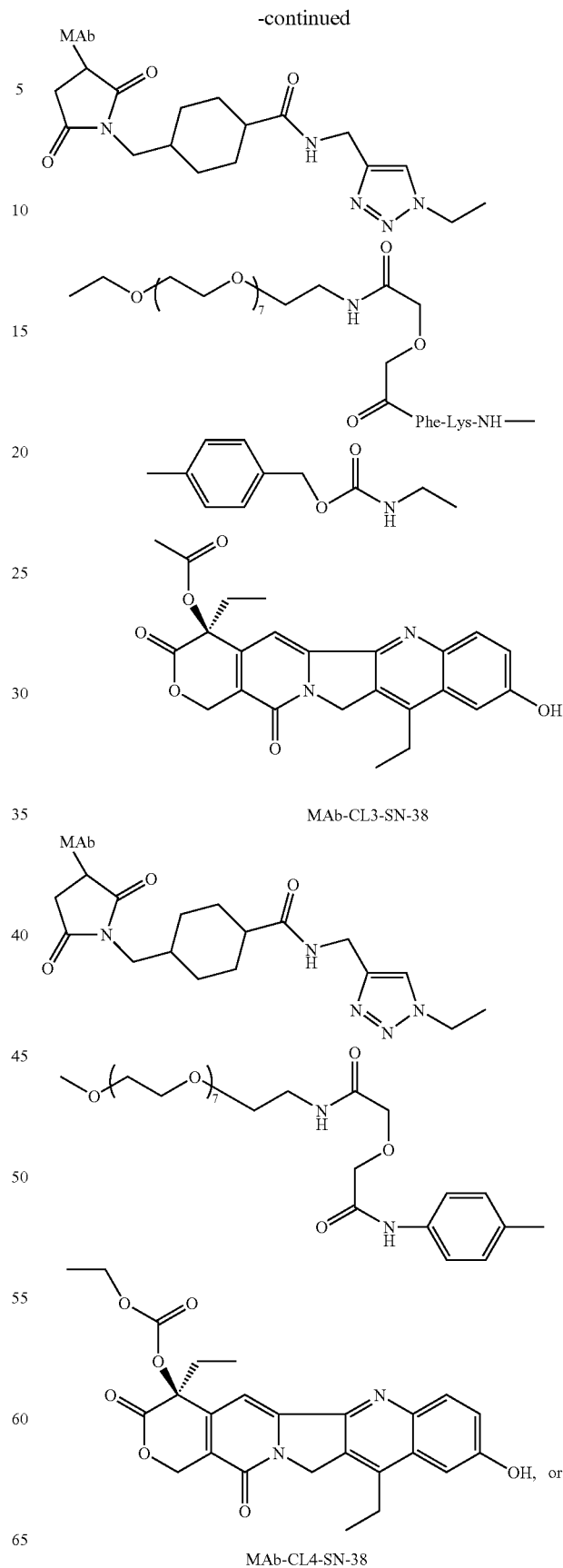
MAb-CL3-SN-38
MAb-CL4-SN-38

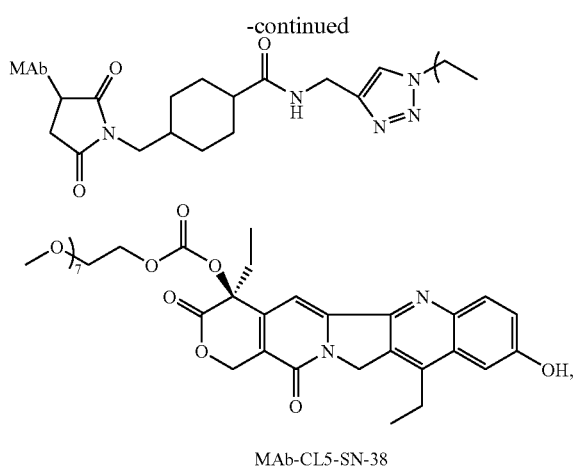

MAb-CL5-SN-38 wherein said MAb is selected from the group consisting of a murine, chimeric, primatized, humanized, or human monoclonal antibody, and said antibody is in intact, fragment (Fab, Fab', F(ab)2, F(ab')2), or sub-fragment (single-chain construct) form.

2. The conjugate according to claim 1, wherein said antibody or antibody fragment is an IgG1, IgG2a, IgG3 or IgG4.

3. The conjugate according to claim 1, wherein said MAb is an internalizing antibody.

4. The conjugate according to claim 1, wherein said antibody is attached to between 1 and 12 CPT moieties.

5. The conjugate according to claim 1, wherein the antibody or fragment thereof binds to an antigen expressed by or associated with a cancer.

6. The conjugate according to claim 5, wherein the cancer is selected from the group consisting of testicular cancer, myeloid leukemia, B-cell lymphomas, B-cell leukemias, chronic lymphocytic leukemia, T-cell lymphomas, non-Hodgkin's lymphoma, Hodgkin's disease, prostate cancer, breast cancer, ovarian cancer, stomach cancer, bladder cancer, non-small-cell lung cancer, glioblastoma, colorectal cancer, pancreatic cancer, head and neck squamous cell carcinoma, multiple myeloma, melanoma, lung cancer, renal cancer, glioblastome multiforme, histiocytoma, myeloid leukemia, adenocarcinomas, sarcomas, glial tumors and hepatocellular carcinoma.

7. The conjugate according to claim 1, wherein the 10-hydroxy position of SN-38 is protected as 10-O-ester or 10-O-carbonate derivative using a 'COR' moiety where the R group is selected from substituted alkyl residue such as "N(CH$_3$)$_2$—(CH$_2$)$_n$—" where n is 2-10 and wherein the terminal amino group is optionally in the form of a quaternary salt for enhanced aqueous solubility, or simple alkyl residue such as "CH$_3$—(CH$_2$)$_n$—" where n is 0-10, or alkoxy residues such as "CH$_3$—(CH$_2$)$_n$—O—" where n is 0-10 or "N(CH$_3$)$_2$—(CH$_2$)$_n$—O—" where n is 2-10, or "R$_1$O—(CH$_2$—CH$_2$—O)$_n$—CH$_2$—CH$_2$—O—" where R$_1$ is ethyl or methyl and n is an integer with values of 0-10.

8. The conjugate according to claim 1, wherein said MAb binds to an antigen selected from the group consisting of CD74, CD22, epithelial glycoprotein-1, carcinoembryonic antigen (CEA or CD66e), colon-specific antigen-p, alpha-fetoprotein, CC49, prostate-specific membrane antigen (PSMA), carbonic anhydrase IX, HER-2/neu, EGFR (ErbB1), ErbB2, ErbB3, ILGF, BrE3, CD19, CD20, CD21, CD23, CD33, CD38, CD40, CD44, CD45, CD79a, CD79b, CD80, CD133, CD138, VEGF, ED-B fibronectin, PlGF, a tumor angiogenesis antigen, MUC1, MUC2, MUC3, MUC4, gangliosides, HCG, EGP-2, CD37, HLA-DR, CD30, Ia, A3, A33, Ep-CAM, KS-1, Le(y), S100, PSA, tenascin, testis antigens, folate receptor, Thomas-Friedreich antigens, tumor necrosis antigens, Ga 733, IL-2, IL-6, T101, MAGE, macrophage migration inhibitory factor (MIF), an antigen that is bound by L243, an antigen that is bound by PAM4, CD66a (BGP), CD66b (CGM6), CD66c (NCA), CD66d (CGM1), TAC, cancer stem-cell antigens and combinations thereof.

9. The conjugate according to claim 1, wherein said MAb is multispecific, with multiple binding arms to target at least two different antigens or epitopes contained on the target cell or pathogen, and one or more targeting arms are conjugated to CPT.

10. The conjugate of claim 9, wherein said multispecific antibody binds to two or more antigens selected from the group consisting of CD74, CD22, epithelial glycoprotein-1, carcinoembryonic antigen (CEA or CD66e), colon-specific antigen-p, alpha-fetoprotein, CC49, prostate-specific membrane antigen (PSMA), carbonic anhydrase IX, HER-2/neu, ILGF, BrE3, CD19, CD20, CD21, CD23, CD33, CD38, CD40, CD44, CD45, CD79a, CD79b, CD80, CD133, CD138, VEGF, EGF receptor (ErbB1), ErbB2, ErbB3, PlGF, VFGF, ED-B fibronectin, MUC1, MUC2, MUC3, MUC4, Tag-72, ILGF, gangliosides, HCG, EGP-2, CD37, HLA-DR, CD30, Ia, A3, A33, Ep-CAM, KS-1, Le(y), S100, PSA, tenascin, testis antigen, folate receptor, Thomas-Friedreich antigens, tumor necrosis antigens, tumor angiogenesis antigens, MIF, Ga 733, IL-2, IL-6, T101, MAGE, an antigen that is bound by L243, an antigen that is bound by PAM4, CD66a (BGP), CD66b (CGM6), CD66c (NCA), CD66d (CGM1), TAC, and cancer stem-cell antigens.

11. The conjugate of claim 1, wherein the antibody fragment is a fusion protein.

12. The conjugate of claim 11, wherein the fusion protein is constructed by the 'dock and lock' technology.

13. The conjugate of claim 1, wherein said conjugate is in a form suitable for parenteral administration.

14. A process for producing the conjugate of claim 1, wherein a linker is first conjugated to the CPT-drug, thereby producing a CPT drug-linker conjugate, and wherein said CPT drug-linker conjugate is subsequently conjugated to a MAb.

* * * * *